US009434928B2

(12) United States Patent
Mendell et al.

(10) Patent No.: US 9,434,928 B2
(45) Date of Patent: Sep. 6, 2016

(54) RECOMBINANT ADENO-ASSOCIATED VIRUS DELIVERY OF ALPHA-SARCOGLYCAN POLYNUCLEOTIDES

(71) Applicant: NATIONWIDE CHILDREN'S HOSPITAL, INC., Columbus, OH (US)

(72) Inventors: Jerry R. Mendell, Columbus, OH (US); Louis Chicoine, Westerville, OH (US); Louise Rodino-Klapac, Groveport, OH (US); Kelly Reed Clark, Columbus, OH (US); Thomas J. Preston, Groveport, OH (US)

(73) Assignee: NATIONWIDE CHILDREN'S HOSPITAL, INC., Columbus, OH (US)

( * ) Notice: Subject to any disclaimer, the term of this patent is extended or adjusted under 35 U.S.C. 154(b) by 0 days.

(21) Appl. No.: 14/360,243

(22) PCT Filed: Nov. 21, 2012

(86) PCT No.: PCT/US2012/066265
§ 371 (c)(1),
(2) Date: May 22, 2014

(87) PCT Pub. No.: WO2013/078316
PCT Pub. Date: May 30, 2013

(65) Prior Publication Data
US 2014/0323956 A1 Oct. 30, 2014

Related U.S. Application Data

(60) Provisional application No. 61/563,139, filed on Nov. 23, 2011.

(51) Int. Cl.
| | | |
|---|---|---|
| *A61P 21/00* | (2006.01) | |
| *A61K 35/76* | (2015.01) | |
| *C07K 14/015* | (2006.01) | |
| *C12N 7/00* | (2006.01) | |
| *A61K 48/00* | (2006.01) | |
| *A61M 1/36* | (2006.01) | |
| *A61M 5/14* | (2006.01) | |

(52) U.S. Cl.
CPC .............. *C12N 7/00* (2013.01); *A61K 48/005* (2013.01); *A61K 48/0075* (2013.01); *A61M 1/3603* (2014.02); *A61M 5/1408* (2013.01); *C12N 2750/14143* (2013.01)

(58) Field of Classification Search
None
See application file for complete search history.

(56) References Cited

U.S. PATENT DOCUMENTS

| | | |
|---|---|---|
| 5,173,414 A | 12/1992 | Lebkowski et al. |
| 5,449,616 A | 9/1995 | Campbell et al. |
| 5,658,776 A | 8/1997 | Flotte et al. |
| 5,786,211 A | 7/1998 | Johnson |
| 5,871,982 A | 2/1999 | Wilson et al. |
| 6,258,595 B1 | 7/2001 | Gao et al. |
| 6,262,035 B1 | 7/2001 | Campbell et al. |
| 6,566,118 B1 | 5/2003 | Atkinson et al. |
| 7,282,199 B2 | 10/2007 | Gao et al. |
| 2009/0054823 A1 | 2/2009 | Bridges et al. |
| 2009/0275107 A1 | 11/2009 | Lock et al. |
| 2009/0280103 A1 | 11/2009 | Flueck |
| 2011/0053221 A1 | 3/2011 | Chen et al. |
| 2011/0070210 A1 | 3/2011 | Andrijauskas |

FOREIGN PATENT DOCUMENTS

| | | |
|---|---|---|
| WO | WO-95/13365 A1 | 5/1995 |
| WO | WO-95/13392 A1 | 5/1995 |
| WO | WO-96/17947 A1 | 6/1996 |
| WO | WO-97/06243 A1 | 2/1997 |
| WO | WO-97/08298 A1 | 3/1997 |
| WO | WO-97/09441 A2 | 3/1997 |
| WO | WO-97/21825 A1 | 6/1997 |
| WO | WO-98/09657 A2 | 3/1998 |
| WO | WO-99/11764 A2 | 3/1999 |
| WO | WO-01/83692 A2 | 11/2001 |

OTHER PUBLICATIONS

Wang et al., Gene Therapy (2003) 10, 1528-1534 Recombinant AAV serotype 1 transduction efficiency and tropism in the murine brain.*
Mendell et al., Ann Neurol. Sep. 2009;66(3):290-7 Limb-girdle muscular dystrophy type 2D gene therapy restores alpha-sarcoglycan and associated proteins.*
McCarty et al., Adeno-associated virus terminal repeat (TR) mutant generates self-complementary vectors to overcome the rate-limiting step to transduction in vivo Gene Therapy (2003) 10, 2112-2118.*
Allamand et al., Early adenovirus-mediated gene transfer effectively prevents muscular dystrophy in alpha-sarcoglycan-deficient mice, Gene Ther., 7(16):1385-91 (2000).
Carter, Adeno-associated virus vectors, Curr. Opin. Biotechnol., 1533-539 (1992).
Clark et al., A stable cell line carrying adenovirus-inducible rep and cap genes allows for infectivity titration of adeno-associated virus vectors, Gene Ther., 3(12):1124-32 (1996).
Clark et al., Highly purified recombinant adeno-associated virus vectors are biologically active and free of detectable helper and wild-type viruses, Hum. Gene Ther., 10(6)1031-9 (1999).
Cserjesi et al., Myogenin induces the myocyte-specific enhancer binding factor MEF-2 independently of other muscle-specific gene products, Mol. Cell Biol., 11(10):4854-62 (1991).
De et al., High levels of persistent expression of alpha1-antitrypsin mediated by the nonhuman primate serotype rh.10 adeno-associated virus despite preexisting immunity to common human adeno-associated viruses, Mol. Ther., 13(1):67-76 (2006).

(Continued)

Primary Examiner — Maria Leavitt
(74) Attorney, Agent, or Firm — Marshall, Gerstein & Borun LLP

(57) ABSTRACT

The present invention relates to recombinant adeno-associated virus (rAAV) delivery of an alpha-sarcoglycan gene. The invention provides rAAV products and methods of using the rAAV in the treatment of limb girdle muscular dystrophies such as LGMD2D.

7 Claims, 23 Drawing Sheets

(56) References Cited

OTHER PUBLICATIONS

Gao et al., Clades of Adeno-associated viruses are widely disseminated in human tissues, J. Virol., 78(12):6381-8 (2004).
Hermonat et al., Use of adeno-associated virus as a mammalian DNA cloning vector: transduction of neomycin resistance into mammalian tissue culture cells, Proc. Natl. Acad. Sci. USA, 81(20):6466-70 (1984).
International Preliminary Report on Patentability, corresponding International Application No. PCT/US2012/066265, May 27, 2014.
International Search Report and Written Opinion, corresponding International Application No. PCT/US12/66265, Mar. 28, 2013 (mailing date).
Johnson et al., Muscle creatine kinase sequence elements regulating skeletal and cardiac muscle expression in transgenic mice, Mol. Cell Biol., 9(8):3393-9 (1989).
Justison et al., Percutaneous assisted venous return isolated limb perfusion, J. Extra Corpor. Technol., 41(4):231-4 (2009).
Laughlin et al., Cloning of infectious adeno-associated virus genomes in bacterial plasmids, Gene, 23(1):65-73 (1983).
Lebkowski et al., Adeno-associated virus: a vector system for efficient introduction and integration of DNA into a variety of mammalian cell types, Mol. Cell Biol., 8:3988-96 (1988).
Mader et al., A steroid-inducible promoter for the controlled overexpression of cloned genes in eukaryotic cells, Proc. Natl. Acad. Sci. USA, 90(12):5603-7 (1993).
Martin et al., Overexpression of Galgt2 in skeletal muscle prevents injury resulting from eccentric contractions in both mdx and wild-type mice, Am. J. Physiol. Cell Physiol., 296:C476-88 (2009).
McLaughlin et al., Adeno-associated virus general transduction vectors: analysis of proviral structures, J. Virol., 62(6):1963-73 (1988).
Mendell et al., Sustained alpha-sarcoglycan gene expression after gene transfer in limb-girdle muscular dystrophy, type 2D, Ann. Neurol., 68(5):629-38 (2010).
Muscat et al., Multiple 5'-flanking regions of the human alpha-skeletal actin gene synergistically modulate muscle-specific expression, Mol. Cell Biol., 7(11):4089-99 (1987).
Muzyczka, Use of adeno-associated virus as a general transduction vector for mammalian cells, Curr. Top Microbiol. Immunol., 158:97-129 (1992).
Pacak et al., Long-term skeletal muscle protection after gene transfer in a mouse model of LGMD-2D, Mol. Ther., 15(10):1775-81 (2007).
Paul et al., Increased viral titer through concentration of viral harvests from retroviral packaging lines, Hum. Gene Ther., 4(5):609-15 (1993).
Perrin et al., An experimental rabies vaccine produced with a new BHK-21 suspension cell culture process: use of serum-free medium and perfusion-reactor system, Vaccine, 13(13):1244-50 (1995).

Rabinowitz et al., Cross-packaging of a single adeno-associated virus (AAV) type 2 vector genome into multiple AAV serotypes enables transduction with broad specificity, J. Virol., 76(2):791-801 (2002).
Rodino-Klapac et al., A translational approach for limb vascular delivery of the micro-dystrophin gene without high volume or high pressure for treatment of Duchenne muscular dystrophy, J. Transl. Med., 5:45 (2007).
Rodino-Klapac et al., Lack of toxicity of alpha-sarcoglycan overexpression supports clinical gene transfer trial in LGMD2D, Neurology, 71(4):240-7 (2008).
Rodino-Klapac et al., Persistent expression of FLAG-tagged micro dystrophin in nonhuman primates following intramuscular and vascular delivery, Mol. Ther., 18(1)109-17 (2010).
Samulski et al., Cloning of adeno-associated virus into pBR322: rescue of intact virus from the recombinant plasmid in human cells, Proc. Natl. Acad. Sci. USA, 79(6):2077-81 (1982).
Samulski et al., Helper-free stocks of recombinant adeno-associated viruses: normal integration does not require viral gene expression, J. Virol., 63(9):3822-8 (1989).
Schnepp et al., Highly purified recombinant adeno-associated virus vectors. Preparation and quantitation, Methods Mol. Med., 69:427-43 (2002).
Semenza et al., Hypoxia-inducible nuclear factors bind to an enhancer element located 3' to the human erythropoietin gene, Proc. Natl. Acad. Sci. USA, 88(13):5680-4 (1991).
Senapathy et al., Molecular cloning of adeno-associated virus variant genomes and generation of infectious virus by recombination in mammalian cells, J. Biol. Chem., 259(7):4661-6 (1984).
Srivastava et al., Nucleotide sequence and organization of the adeno-associated virus 2 genome, J. Virol., 45(2):555-64 (1983).
Tratschin et al., Adeno-associated virus vector for high-frequency integration, expression, and rescue of genes in mammalian cells, Mol. Cell Biol., 5(11):3251-60 (1985).
van Akkooi et al., Isolated limb perfusion for an irresectable melanoma recurrence in a Jehovah's witness, Eur. J. Cardiothorac. Surg., 30(2):408-10 (2006).
Wang et al., Recombinant AAV serotype 1 transduction efficiency and tropism in the murine brain, Gene Ther., 10(17):1528-34 (2003).
Weintraub et al., The myoD gene family: nodal point during specification of the muscle cell lineage, Science, 251(4995):761-6 (1991).
Xu et al., Postnatal overexpression of the CT GalNAc transferase inhibits muscular dystrophy in mdx mice without altering muscle growth or neuromuscular development: evidence for a utrophin-independent mechanism, Neuromuscul. Disord., 17(3):209-20 (2007).

\* cited by examiner

Figure 1

```
Lipman-Pearson Protein Alignment

Ktuple: 2;   Gap Penalty: 4;   Gap Length Penalty: 12

Seq1(1>738)        Seq2(1>739)         Similarity    Gap       Gap        Consensus AAV 8 cap          rh74 (AAV8) aa      Index         Number    Length     Length (1>738)            (1>738)             93.4          0         0          738 v10        v20        v30        v40        v50        v60

MAADGYLPDWLEDNLSEGIREWWALKPGAPKPKANQQKQDDGRGLVLPGYKYLGPFNGLD

MAADGYLPDWLEDNLSEGIREWW.LKPGAPKPKANQQKQD:GRGLVLPGYKYLGPFNGLD

MAADGYLPDWLEDNLSEGIREWWDLKPGAPKPKANQQKQDNGRGLVLPGYKYLGPFNGLD

^10        ^20        ^30        ^40        ^50        ^60 v70        v80        v90        v100       v110       v120

KGEPVNAADAAALEHDKAYDQQLQAGDNPYLRYNHADAEFQERLQEDTSFGGNLGRAVFQ

KGEPVNAADAAALEHDKAYDQQLQAGDNPYLRYNHADAEFQERLQEDTSFGGNLGRAVFQ

KGEPVNAADAAALEHDKAYDQQLQAGDNPYLRYNHADAEFQERLQEDTSFGGNLGRAVFQ

^70        ^80        ^90        ^100       ^110       ^120 v130       v140       v150       v160       v170       v180

AKKRVLEPLGLVEEGAKTAPGKKRPVEPSPQRSPDSSTGIGKKGQQPARKRLNFGQTGDS

AKKRVLEPLGLVE..KTAPGKKRPVEPSPQRSPDSSTGIGKKGQQPA:KRLNFGQTGDS

AKKRVLEPLGLVESPVKTAPGKKRPVEPSPQRSPDSSTGIGKKGQQPAKKRLNFGQTGDS

^130       ^140       ^150       ^160       ^170       ^180 v190       v200       v210       v220       v230       v240

ESVPDPQPLGEPPAAPSGVGPNTMAAGGGAPMADNNEGADGVGSSSGNWHCDSTWLGDRV

ESVPDPQP:GEPPA:PSG:G:.TMAAGGGAPMADNNEGADGVGSSSGNWHCDSTWLGDRV

ESVPDPQPIGEPPAGPSGLGSGTMAAGGGAPMADNNEGADGVGSSSGNWHCDSTWLGDRV

```
        v250      v260      v270      v280      v290      v300
ITTSTRTWALPTYNNHLYKQISNGTSGGATNDNTYFGYSTPWGYFDFNRFHCHFSPRDWQ
ITTSTRTWALPTYNNHLYKQISNGTSGG:TNDNTYFGYSTPWGYFDFNRFHCHFSPRDWQ
ITTSTRTWALPTYNNHLYKQISNGTSGGSTNDNTYFGYSTPWGYFDFNRFHCHFSPRDWQ
        ^250      ^260      ^270      ^280      ^290      ^300 v310      v320      v330      v340      v350      v360
RLINNNWGFRPKRLSFKLFNIQVKEVTQNEGTKTIANNLTSTIQVFTDSEYQLPYVLGSA
RLINNNWGFRPKRL:FKLFNIQVKEVTQNEGTKTIANNLTSTIQVFTDSEYQLPYVLGSA
RLINNNWGFRPKRLNFKLFNIQVKEVTQNEGTKTIANNLTSTIQVFTDSEYQLPYVLGSA
        ^310      ^320      ^330      ^340      ^350      ^360 v370      v380      v390      v400      v410      v420
HQGCLPPFPADVFMIPQYGYLTLNNGSQAVGRSSFYCLEYFPSQMLRTGNNFQFTYTFED
HQGCLPPFPADVFMIPQYGYLTLNNGSQAVGRSSFYCLEYFPSQMLRTGNNF:F:Y.FED
HQGCLPPFPADVFMIPQYGYLTLNNGSQAVGRSSFYCLEYFPSQMLRTGNNFEFSYNFED
        ^370      ^380      ^390      ^400      ^410      ^420 v430      v440      v450      v460      v470      v480
VPFHSSYAHSQSLDRLMNPLIDQYLYYLSRTQTTGGTANTQTLGFSQGGPNTMANQAKNW
VPFHSSYAHSQSLDRLMNPLIDQYLYYLSRTQ:TGGTA.TQ L FSQ:GPN.M:.QAKNW
VPFHSSYAHSQSLDRLMNPLIDQYLYYLSRTQSTGGTAGTQQLLFSQAGPNNMSAQAKNW
        ^430      ^440      ^450      ^460      ^470      ^480 v490      v500      v510      v520      v530      v540
LPGPCYRQQRVSTTTGQNNNSNFAWTAGTKYHLNGRNSLANPGIAMATHKDDEERFFPSN
LPGPCYRQQRVSTT :QNNNSNFAWT::TKYHLNGR:SL.NPG:AMATHKDDEERFFPS:
LPGPCYRQQRVSTTLSQNNNSNFAWTGATKYHLNGRDSLVNPGVAMATHKDDEERFFPSS
        ^490      ^500      ^510      ^520      ^530      ^540 v550      v560      v570      v580      v590      v600
GILIFGKQNAARDNADYSDVMLTSEEEIKTTNPVATEEYGIVADNLQQQNTAPQIGTVNS
G:L:FGKQ.A::DN.DYS.VMLTSEEEIKTTNPVATE:YG:VADNLQQQN:AP :G:VNS
GVLMFGKQGAGKDNVDYSSVMLTSEEEIKTTNPVATEQYGVVADNLQQQNAAPIVGAVNS
        ^550      ^560      ^570      ^580      ^590      ^600
```

Figure 1 Continued...

```
     v610      v620      v630      v640      v650      v660
QGALPGMVWQNRDVYLQGPIWAKIPHTDGNFHPSPLMGGFGLKHPPPQILIKNTPVPADP

QGALPGMVWQNRDVYLQGPIWAKIPHTDGNFHPSPLMGGFGLKHPPPQILIKNTPVPADP

QGALPGMVWQNRDVYLQGPIWAKIPHTDGNFHPSPLMGGFGLKHPPPQILIKNTPVPADP
     ^610      ^620      ^630      ^640      ^650      ^660 v670      v680      v690      v700      v710      v720
PTTFNQSKLNSFITQYSTGQVSVEIEWELQKENSKRWNPEIQYTSNYYKSTSVDFAVNTE

PTTFNQ:KL.SFITQYSTGQVSVEIEWELQKENSKRWNPEIQYTSNYYKST:VDFAVNTE

PTTFNQAKLASFITQYSTGQVSVEIEWELQKENSKRWNPEIQYTSNYYKSTNVDFAVNTE
     ^670      ^680      ^690      ^700      ^710      ^720 v730
GVYSEPRPIGTRYLTRNL

G.YSEPRPIGTRYLTRNL

GTYSEPRPIGTRYLTRNL
     ^730
```

Figure 4

```
5'  CTCCATCACTAGGGGTAACCGCGAAGCGCCTCCCACGCTGCCGCGTCAGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  50
    ←――――――D――――――→

5'  GCTGACGTAAATTACGTCATAGGGGAGTGGTCCTGTATTAGCTGTCACGT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  100

5'  GAGTGCTTTTGCGACATTTTGCGACACCACGTGGCCATTCATGGTATATA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  150
                                              TAT box 5'  TGGCCGAGTGAGCGAGCAGGATCTCCATTTTGACCGCGAAATTTGAACGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  200
    ▓              p_9tet 5'  GCAGCAGCCATGCCGGGCTTCTACGAGATCGTGCTTAAGGTGCCGAGCGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  250
                          Rep 5'  CCTGGACGAGCACCTGCCGGGCATTTCTGACTCGTTTGTGAACTGGGTGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  300
                          Rep 5'  CAGAGAAGGAATGGGAGCTGCCCCCGGATTCTGACATGGATCGGAATCTG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  350
                          Rep 5'  ATTGAGCAGGCACCCCTGACCGTGGCCGAGAAGCTACAGCGCGACTTCCT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  400
                          Rep 5'  GGTCCAATGGCGCCGCGTGAGTAAGGCCCCGGAGGCCCTCTTCTTTGTTC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  450
                          Rep 5'  AGTTCGAGAAGGGCGAGTCCTACTTCCACCTCCATATTCTGGTAGAGACC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  500
                          Rep
```

Figure 4 Continued...

```
5'  ACGGGGGTCAAATCCATGGTGCTGGGCCGCTTCCTGAGTCAGATTCGGGA
                                                        550
                        Rep

5'  CAAGCTGGTGCAGACCATCTACCGCGGGATCGAGCCGACCCTGCCCAACT
                                                        600
                        Rep

5'  GGTTCGCGGTGACAAAGACGCGTAATGGCGCCGGAGGGGGGAACAACGTG
                                                        650
                        Rep

5'  GTGGACGAGTGCTACATCCCCAACTACCTGCTGCCCAAGACTCAGCCCGA
                                                        700
                        Rep

5'  GCTGCAGTGGGCGTGGACTAACATGGAGGAGTATATAAGCGCGTGCTTGA
                                                        750
                        Rep
                                        TATA Box

5'  ACCTGGCCGAGCGCAAACGGCTCGTGGCGCAGCACCTGACCCACGTCAGC
                                                        800
                        Rep
        pL. 1

5'  CAGACCCAGGAGCAGAACAAGGAGAATCTGAACCCGAATTCTGACGCGCC
                                                        850
                        Rep

5'  TGTCATCCGGTCAAAAACCTCCGCGCGCTACATGGAGCTGGTCGGGTGGC
                                                        900
                        Rep
                                        Rep 52 ORF
```

Figure 4 Continued...

```
5'  TGGTGGACCGGGGCATCACCTCCGAGAAGCAGTGGATCCAGGAGGACCAG
                                                        950
              Rep
              Rep 52 ORF

5'  GCCTCGTACATCTCCTTCAACGCCGCCTCCAACTCGCGGTCTCAGATCAA
                                                        1000
              Rep
              Rep 52 ORF

5'  GGCCGCGCTGGACAATGCCGGCAAGATCATGGCGCTGACCAAATCCGCGC
                                                        1050
              Rep
              Rep 52 ORF

5'  CCGACTACCTGGTAGGCCCCGCTCTGCCCGCGGACATTAAATCCAACCGC
                                                        1100
              Rep
              Rep 52 ORF

5'  ATCTACCGCATCCTGGAGCTGAATGGCTACGACCCTGCCTACGCCGGTTC
                                                        1150
              Rep
              Rep 52 ORF

5'  CGTCTTTCTCGGCTGGGCCCAGAAAAAGTTTGGCAAAAGGAACACCATCT
                                                        1200
              Rep
              Rep 52 ORF

5'  GGCTGTTTGGGCCGGCCACCACGGGCAAGACCAACATCGCGGAAGCCATC
                                                        1250
              Rep
              Rep 52 ORF
```

Figure 4 Continued...

```
5' GCCCACGCCGTGCCCTTCTACGGCTGCGTCAACTGGACCAATGAGAACTT
                                                              1300
                        Rep
                      Rep 52 ORF

5' TCCCTTCAACGATTGCGTCGACAAGATGGTGATCTGGTGGGAGGAGGGCA
                                                              1350
                        Rep
                      Rep 52 ORF

5' AGATGACGGCCAAGGTCGTGGAGTCCGCCAAGGCCATTCTCGGCGGCAGC
                                                              1400
                        Rep
                      Rep 52 ORF

5' AACGTGCGCGTGGACCAAAAGTGCAAGTCGTCCGCCCAGATCGATCCCAC
                                                              1450
                        Rep
                      Rep 52 ORF

5' CCCCGTGATCGTCACCTCCAACACCAACATGTGCGCCGTGATTGACGGGA
                                                              1500
                        Rep
                      Rep 52 ORF

5' ACAGCACCACCTTCGAGCACCAGCAGCCGTTGCAGGACCGGATGTTCAAA
                                                              1550
                        Rep
                      Rep 52 ORF

5' TTTGAACTTACCCGCCGTCTGGAGCACGACTTTGGCAAGGTGACAAAGCA
                                                              1600
                        Rep
                      Rep 52 ORF
```

Figure 4 Continued...

```
5' GGAAGTCAAAGAGTTCTTCCGCTGGGCGCAGGATCACGTGACCGAGGTGG
                                                          1650
                         Rep
                      Rep 52 ORF

5' CGCATGAGTTCTACGTCAGAAAGGGTGGAGCTAACAAAAGACCCGCCCCC
                                                          1700
                         Rep
                      Rep 52 ORF

5' GATGACGGGGATATAAGCGAGCCCAAGCGGGCCTGCCCCTCAGTCGCGGA
                                                          1750
                         Rep
                      Rep 52 ORF
             p40_px

5' TCCATCGACGTCAGACGCGGAAGGAGCTCCGGTGGACTTTGCCGACAGGT
                                                          1800
                         Rep
                      Rep 52 ORF
                                                   Sp_r

5' ACCAAAACAAATGTTCTCGTCACGCGGGCATGCTTCAGATGCTGTTTCCC
                                                          1850
                         Rep
                      Rep 52 ORF

5' TGCAAAACATGCGAGAGAATGAATCAGAATTTCAACATTTGCTTCACGCA
                                                          1900
                         Rep
                      Rep 52 ORF

5' CGGGACCAGAGACTGTTCAGAATGTTTCCCTGGCGTGTCAGAATCTCAAC
                                                          1950
                         Rep
                      Rep 52 ORF
```

Figure 4 Continued...

```
5'  CGGTCGTCAGAAAAAGACGTATCGGAAACTCTGTGCGATTCATCATCTG
                                                              2000
                            Rep
                         Rep 52 ORF

5'  CTGGGGCGGGCACCCGAGATTGCTTGCTCGGCCTGCGACCTGGTCAACGT
                                                              2050
                            Rep
                         Rep 52 ORF

5'  GGACCTGGATGACTGTGTTTCTGAGCAATAAATGACTTAAACCAGGTATG
                                                              2100
                            Rep
                                                        Cap
                      Rep 52 ORF
                                    R
                                              sp...r

5'  GCTGCCGATGGTTATCTTCCAGATTGGCTCGAGGACAACCTCTCTGACGG
                                                              2150
                            Rep
                            Cap
                          sp..r
                                              R

5'  CATTCGCGAGTGGTGGGACCTGAAACCTGGAGCCCCGAAACCCAAAGCCA
                                                              2200
                            Cap

5'  ACCAGCAAAAGCAGGACAACGGCCGGGGTCTGGTGCTTCCTGGCTACAAG
                                                              2250
                            Cap

5'  TACCTCGGACCCTTCAACGGACTCGACAAGGGGGAGCCCGTCAACGCGGC
                                                              2300
                            Cap
```

Figure 4 Continued...

```
5' GGACGCAGCGGCCCTCGAGCACGACAAGGCCTACGACCAGCAGCTCCAAG
                                                              2350
                          Cap

5' CGGGTGACAATCCGTACCTGCGGTATAATCACGCCGACGCCGAGTTTCAG
                                                              2400
                          Cap

5' GAGCGTCTGCAAGAAGATACGTCTTTTGGGGGCAACCTCGGGCGCGCAGT
                                                              2450
                          Cap

5' CTTCCAGGCCAAAAAGCGGGTTCTCGAACCTCTGGGCCTGGTTGAATCGC
                                                              2500
                          Cap

5' CGGTTAAGACGGCTCCTGGAAAGAAGAGACCGGTAGAGCCATCACCCCAG
                                                              2550
                          Cap
        VP1

5' CGCTCTCCAGACTCCTCTACGGGCATCGGCAAGAAAGGCCAGCAGCCCGC
                                                              2600
                          Cap

5' AAAAAAGAGACTCAATTTTGGGCAGACTGGCGACTCAGAGTCAGTCCCCG
                                                              2650
                          Cap

5' ACCCTCAACCAATCGGAGAACCACCAGCAGGCCCCTCTGGTCTGGGATCT
                                                              2700
                          Cap

5' GGTACAATGGCTGCAGGCGGTGGCGCTCCAATGGCAGACAATAACGAAGG
                                                              2750
                          Cap
        VP3
```

Figure 4 Continued...

```
5'  CGCCGACGGAGTGGGTAGTTCCTCAGGAAATTGGCATTGCGATTCCACAT
    ++++++++++++++++++++++++++++++++++++++++++++++++++  2800
                           Cap

5'  GGCTGGGCGACAGAGTCATCACCACCAGCACCCGCACCTGGGCCCTGCCC
    ++++++++++++++++++++++++++++++++++++++++++++++++++  2850
                           Cap

5'  ACCTACAACAACCACCTCTACAAGCAAATCTCCAACGGGACCTCGGGAGG
    ++++++++++++++++++++++++++++++++++++++++++++++++++  2900
                           Cap

5'  AAGCACCAACGACAACACCTACTTCGGCTACAGCACCCCCTGGGGGTATT
    ++++++++++++++++++++++++++++++++++++++++++++++++++  2950
                           Cap

5'  TTGACTTCAACAGATTCCACTGCCACTTTTCACCACGTGACTGGCAGCGA
    ++++++++++++++++++++++++++++++++++++++++++++++++++  3000
                           Cap

5'  CTCATCAACAACAACTGGGGATTCCGGCCCAAGAGGCTCAACTTCAAGCT
    ++++++++++++++++++++++++++++++++++++++++++++++++++  3050
                           Cap

5'  CTTCAACATCCAAGTCAAGGAGGTCACGCAGAATGAAGGCACCAAGACCA
    ++++++++++++++++++++++++++++++++++++++++++++++++++  3100
                           Cap

5'  TCGCCAATAACCTTACCAGCACGATTCAGGTCTTTACGGACTCGGAATAC
    ++++++++++++++++++++++++++++++++++++++++++++++++++  3150
                           Cap

5'  CAGCTCCCGTACGTGCTCGGCTCGGCGCACCAGGGCTGCCTGCCTCCGTT
    ++++++++++++++++++++++++++++++++++++++++++++++++++  3200
                           Cap
```

Figure 4 Continued...

```
5'  CCCGGCGGACGTCTTCATGATTCCTCAGTACGGGTACCTGACTCTGAACA
                                                        3250
                          Cap

5'  ATGGCAGTCAGGCTGTGGGCCGGTCGTCCTTCTACTGCCTGGAGTACTTT
                                                        3300
                          Cap

5'  CCTTCTCAAATGCTGAGAACGGGCAACAACTTTGAATTCAGCTACAACTT
                                                        3350
                          Cap

5'  CGAGGACGTGCCCTTCCACAGCAGCTACGCGCACAGCCAGAGCCTGGACC
                                                        3400
                          Cap

5'  GGCTGATGAACCCTCTCATCGACCAGTACTTGTACTACCTGTCCCGGACT
                                                        3450
                          Cap

5'  CAAAGCACGGGCGGTACTGCAGGAACTCAGCAGTTGCTATTTTCTCAGGC
                                                        3500
                          Cap

5'  CGGGCCTAACAACATGTCGGCTCAGGCCAAGAACTGGCTACCCGGTCCCT
                                                        3550
                          Cap

5'  GCTACCGGCAGCAACGCGTCTCCACGACACTGTCGCAGAACAACAACAGC
                                                        3600
                          Cap

5'  AACTTTGCCTGGACGGGTGCCACCAAGTATCATCTGAATGGCAGAGACTC
                                                        3650
                          Cap
```

Figure 4 Continued...

```
5'  TCTGGTGAATCCTGGCGTTGCCATGGCTACCCACAAGGACGACGAAGAGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3700
                          Cap

5'  GATTTTTTCCATCCAGCGGAGTCTTAATGTTTGGGAAACAGGGAGCTGGA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3750
                          Cap

5'  AAAGACAACGTGGACTATAGCAGCGTGATGCTAACCAGCGAGGAAGAAAT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3800
                          Cap

5'  AAAGACCACCAACCCAGTGGCCACAGAACAGTACGGCGTGGTGGCCGATA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3850
                          Cap

5'  ACCTGCAACAGCAAAACGCCGCTCCTATTGTAGGGGCCGTCAATAGTCAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3900
                          Cap

5'  GGAGCCTTACCTGGCATGGTGTGGCAGAACCGGGACGTGTACCTGCAGGG
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  3950
                          Cap

5'  TCCCATCTGGGCCAAGATTCCTCATACGGACGGCAACTTTCATCCCTCGC
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4000
                          Cap

5'  CGCTGATGGGAGGCTTTGGACTGAAGCATCCGCCTCCTCAGATCCTGATT
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4050
                          Cap

5'  AAAAACACACCTGTTCCCGCGGATCCTCCGACCACCTTCAATCAGGCCAA
    ┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼┼  4100
                          Cap
```

Figure 4 Continued...

```
5'  GCTGGCTTCTTTCATCACGCAGTACAGTACCGGCCAGGTCAGCGTGGAGA
                                                        4150
                        Cap

5'  TCGAGTGGGAGCTGCAGAAGGAGAACAGCAAACGCTGGAACCCAGAGATT
                                                        4200
                        Cap

5'  CAGTACACTTCCAACTACTACAAATCTACAAATGTGGACTTTGCTGTCAA
                                                        4250
                        Cap

5'  TACTGAGGGTACTTATTCCGAGCCTCGCCCCATTGGCACCCGTTACCTCA
                                                        4300
                        Cap

5'  CCCGTAATCTGTAATTACATGTTAATCAATAAACCGGTTAATTCGTTTCA
                                                        4350
         Cap
              E                poly_nal 5'  GTTGAACTTTGGTCTCCTGTCCTTCTTATCTTATCGGTTACCATAGAAAC
                                                        4400

5'  TGGTTACTTATTAACTGCTTGGTGCGCTTCGCGATAAAAGACTTACGTCA
                                                        4450

5'  TCGGGTTACCCCTAGTGATGGA
                                                        4472
            D
```

Figure 7
A
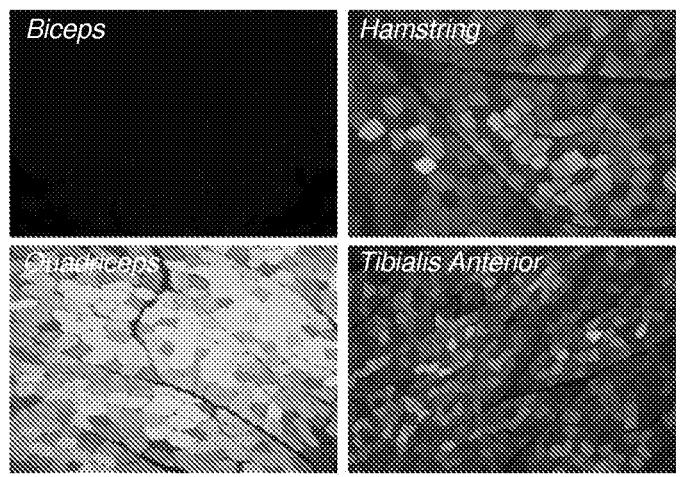
B
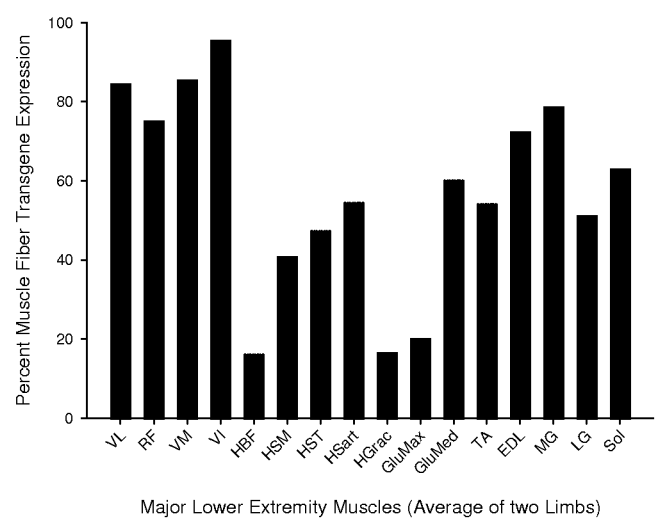

Figure 8
A
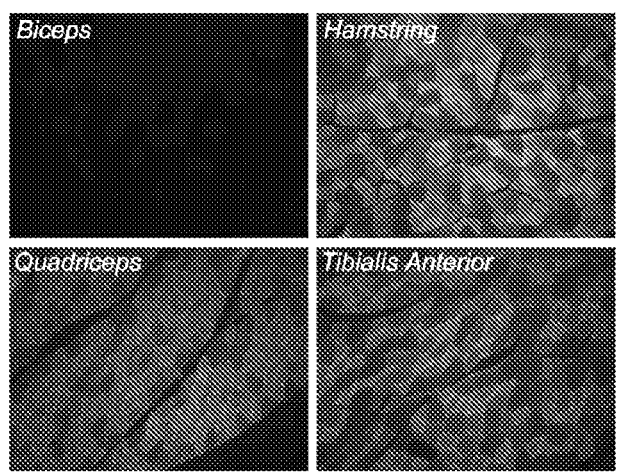
B
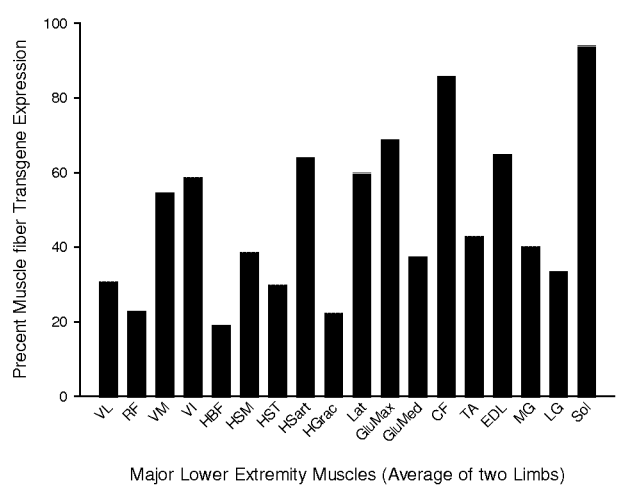

Figure 9
A
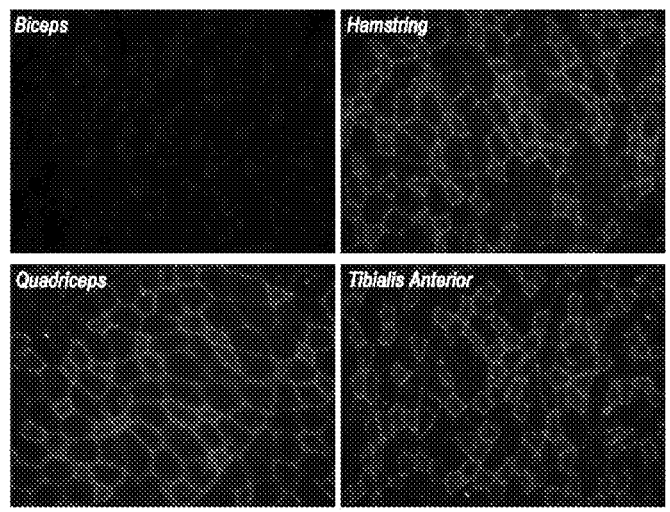
B
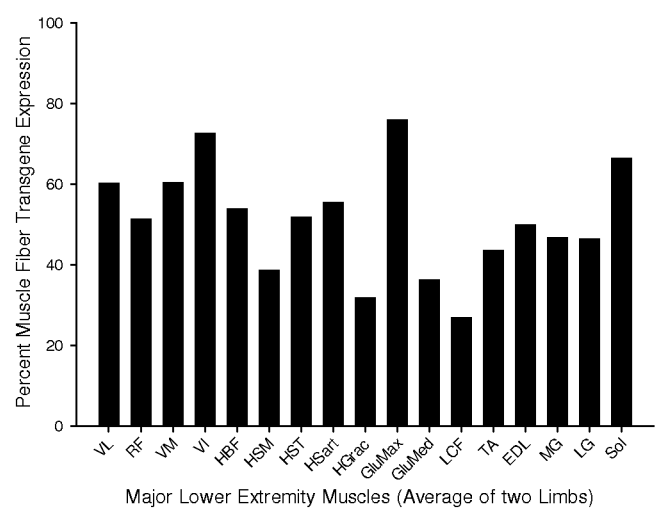

Figure 10
A
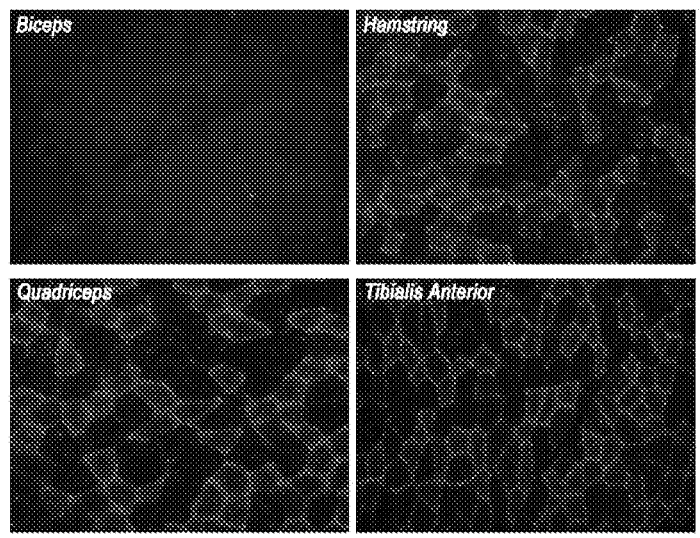
B
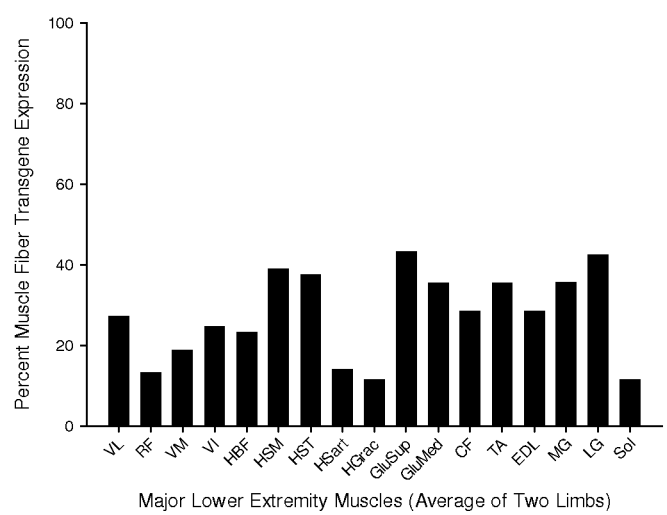

RECOMBINANT ADENO-ASSOCIATED VIRUS DELIVERY OF ALPHA-SARCOGLYCAN POLYNUCLEOTIDES

This application claims the benefit of the filing date of U.S. Provisional Patent Application No. 61/563,139 filed Nov. 23, 2011, which is incorporated by reference herein in its entirety.

STATEMENT OF GOVERNMENT INTEREST

This invention was made with government support under Grant No. 5U54NS055958-03 awarded by the United States National Institute of Health/National Institute of Neurological Disorders and Stroke. The government has certain rights in the invention.

FIELD OF THE INVENTION

The present invention relates to recombinant adeno-associated virus (rAAV) delivery of an alpha-sarcoglycan gene. The invention provides rAAV products and methods of using the rAAV in the treatment of limb girdle muscular dystrophies such as LGMD2D.

INCORPORATION BY REFERENCE OF THE SEQUENCE LISTING

This application contains, as a separate part of disclosure, a Sequence Listing in computer-readable form (filename: 45210PCT_SeqListing.txt; 23,573 byte—ASCII text file) which is incorporated by reference herein in its entirety.

BACKGROUND

Muscular dystrophies (MDs) are a group of genetic diseases. The group is characterized by progressive weakness and degeneration of the skeletal muscles that control movement. Some forms of MD develop in infancy or childhood, while others may not appear until middle age or later. The disorders differ in terms of the distribution and extent of muscle weakness (some forms of MD also affect cardiac muscle), the age of onset, the rate of progression, and the pattern of inheritance.

One group of MDs is the limb girdle group (LGMD) of MDs. LGMDs are rare conditions and they present differently in different people with respect to age of onset, areas of muscle weakness, heart and respiratory involvement, rate of progression and severity. LGMDs can begin in childhood, adolescence, young adulthood or even later. Both genders are affected equally. LGMDs cause weakness in the shoulder and pelvic girdle, with nearby muscles in the upper legs and arms sometimes also weakening with time. Weakness of the legs often appears before that of the arms. Facial muscles are usually unaffected. As the condition progresses, people can have problems with walking and may need to use a wheelchair over time. The involvement of shoulder and arm muscles can lead to difficulty in raising arms over head and in lifting objects. In some types of LGMD, the heart and breathing muscles may be involved.

There are at least nineteen forms of LGMD, and the forms are classified by their associated genetic defects.

| Type | Pattern of Inheritance | Gene or Chromosome |
| --- | --- | --- |
| LGMD1A | Autosomal dominant | Myotilin gene |
| LGMD1B | Autosomal dominant | Lamin A/C gene |
| LGMD1C | Autosomal dominant | Caveolin gene |
| LGMD1D | Autosomal dominant | Chromosome 7 |
| LGMD1E | Autosomal dominant | Chromosome 6 |
| LGMD1F | Autosomal dominant | Chromosome 7 |
| LGMD1G | Autosomal dominant | Chromosome 4 |
| LGMD2A | Autosomal recessive | Calpain-3 gene |
| LGMD2B | Autosomal recessive | Dysferlin gene |
| LGMD2C | Autosomal recessive | Gamma-sarcoglycan gene |
| LGMD2D | Autosomal recessive | Alpha-sarcoglycan gene |
| LGMD2E | Autosomal recessive | Beta-sarcoglycan gene |
| LGMD2F | Autosomal recessive | Delta-sarcoglycan gene |
| LGMD2G | Autosomal recessive | Telethonin gene |
| LGMD2H | Autosomal recessive | TRIM32 |
| LGMD2I | Autosomal recessive | FKRP gene |
| LGMD2J | Autosomal recessive | Titin gene |
| LGMD2K | Autosomal recessive | POMT1 gene |
| LGMD2L | Autosomal recessive | Fukutin gene |

Specialized tests for LGMD are now available through a national scheme for diagnosis, the National Commissioning Group (NCG).

U.S. Pat. No. 6,262,035 states it discloses a method for treating a patient suffering from the disease sarcoglycan-deficient limb-girdle muscular dystrophy by gene replacement therapy. It claims intramuscular injection of an expression vector containing alpha-sarcoglycan nucleic acid. See also, Allamand et al., *Gene Ther.*, 7(16): 1385-1391 (2000).

The present inventors delivered an alpha-sarcoglycan gene in an adeno-associated type 1 vector by intramuscular injection with the goal of treating LGMD2D as described in Rodino-Klapac et al., *Neurology*, 71: 240-247 (2008); Mendell et al., *Ann. Neurol.*, 66(3): 290-297 (2009); and Mendell et al., *Ann. Neurol.*, 68(5): 629-638 (2010).

Adeno-associated virus (AAV) is a replication-deficient parvovirus, the single-stranded DNA genome of which is about 4.7 kb in length including 145 nucleotide inverted terminal repeat (ITRs). There are multiple serotypes of AAV. The nucleotide sequences of the genomes of the AAV serotypes are known. For example, the complete genome of AAV-1 is provided in GenBank Accession No. NC_002077; the complete genome of AAV-2 is provided in GenBank Accession No. NC_001401 and Srivastava et al., J. Virol., 45: 555-564 {1983); the complete genome of AAV-3 is provided in GenBank Accession No. NC_1829; the complete genome of AAV-4 is provided in GenBank Accession No. NC_001829; the AAV-5 genome is provided in GenBank Accession No. AF085716; the complete genome of AAV-6 is provided in GenBank Accession No. NC_00 1862; at least portions of AAV-7 and AAV-8 genomes are provided in GenBank Accession Nos. AX753246 and AX753249, respectively (see also U.S. Pat. Nos. 7,282,199 and 7,790,449 relating to AAV-8); the AAV-9 genome is provided in Gao et al., J. Virol., 78: 6381-6388 (2004); the AAV-10 genome is provided in Mol. Ther., 13(1): 67-76 (2006); and the AAV-11 genome is provided in Virology, 330(2): 375-383 (2004). Cis-acting sequences directing viral DNA replication (rep), encapsidation/packaging and host cell chromosome integration are contained within the AAV ITRs. Three AAV promoters (named p5, p19, and p40 for their relative map locations) drive the expression of the two AAV internal open reading frames encoding rep and cap genes. The two rep promoters (p5 and p19), coupled with the differential splicing of the single AAV intron (at nucleotides 2107 and 2227), result in the production of four rep proteins (rep 78, rep 68, rep 52, and rep 40) from the rep gene. Rep proteins possess multiple enzymatic properties that are ultimately responsible for replicating the viral genome. The cap gene is expressed from the p40 promoter and it encodes the three capsid proteins VP1, VP2, and VP3. Alternative splicing and non-consensus translational start sites are responsible for the production of the three related capsid proteins. A single consensus polyadenylation site is located at map position 95 of the AAV genome. The life cycle and genetics of AAV are reviewed in Muzyczka, Current Topics in Microbiology and Immunology, 158: 97-129 (1992).

AAV possesses unique features that make it attractive as a vector for delivering foreign DNA to cells, for example, in gene therapy. AAV infection of cells in culture is noncytopathic, and natural infection of humans and other animals is silent and asymptomatic. Moreover, AAV infects many mammalian cells allowing the possibility of targeting many different tissues in vivo. Moreover, AAV transduces slowly dividing and non-dividing cells, and can persist essentially for the lifetime of those cells as a transcriptionally active nuclear episome (extrachromosomal element). The AAV proviral genome is infectious as cloned DNA in plasmids which makes construction of recombinant genomes feasible. Furthermore, because the signals directing AAV replication, genome encapsidation and integration are contained within the ITRs of the AAV genome, some or all of the internal approximately 4.3 kb of the genome (encoding replication and structural capsid proteins, rep-cap) may be replaced with foreign DNA. The rep and cap proteins may be provided in trans. Another significant feature of AAV is that it is an extremely stable and hearty virus. It easily withstands the conditions used to inactivate adenovirus (56° to 65° C. for several hours), making cold preservation of AAV less critical. AAV may even be lyophilized. Finally, AAV-infected cells are not resistant to superinfection.

The present inventors have used an AAV8-like AAV termed rh.74 to deliver DNAs encoding various proteins. Xu et al., *Neuromuscular Disorders,* 17: 209-220 (2007) and Martin et al., *Am. J. Physiol. Cell. Physiol.,* 296: 476-488 (2009) relate to rh.74 expression of cytotoxic T cell GalNAc transferase for Duchenne muscular dystrophy. Rodino-Klapac et al., *Mol. Ther.,* 18(1): 109-117 (2010) describes AAV rh.74 expression of a micro-dystrophin FLAG protein tag fusion after delivery of the AAV rh.74 by vascular limb perfusion.

The muscular dystrophies are a group of diseases without identifiable treatment that gravely impact individuals, families, and communities. The costs are incalculable. Individuals suffer emotional strain and reduced quality of life associated with loss of self-esteem. Extreme physical challenges resulting from loss of limb function creates hardships in activities of daily living. Family dynamics suffer through financial loss and challenges to interpersonal relationships. Siblings of the affected feel estranged, and strife between spouses often leads to divorce, especially if responsibility for the muscular dystrophy can be laid at the feet of one of the parental partners. The burden of quest to find a cure often becomes a life-long, highly focused effort that detracts and challenges every aspect of life. Beyond the family, the community bears a financial burden through the need for added facilities to accommodate the handicaps of the muscular dystrophy population in special education, special transportation, and costs for recurrent hospitalizations to treat recurrent respiratory tract infections and cardiac complications. Financial responsibilities are shared by state and federal governmental agencies extending the responsibilities to the taxpaying community.

There thus remains a need in the art for treatments for muscular dystrophies including limb girdle muscular dystrophies such as LGMD2D.

DESCRIPTION

The present invention provides methods and products for preventing, delaying the progression of, and/or treating limb girdle muscular dystrophies. The methods involve vascular delivery (e.g., by limb perfusion including, but not limited to, re-circulating methodology) of an alpha-sarcoglycan expression cassette to muscle cells using AAV as a gene delivery vector. For example, the alpha sarcoglycan expression cassette is inserted in the genome of the AAV referred to as AAV rh.74 herein.

In one aspect, the invention provides an AAV referred to as AAV rh.74. AAV rh.74 exhibits about 93% identity to AAV8 capsid. FIG. 1 provides an alignment of the AAV rh.74 capsid amino acid sequence with the AAV8 capsid amino acid sequence. The polynucleotide and amino acid sequences of the AAV rh.74 capsid are respectively set out in SEQ ID NOs: 1 and 2.

In another aspect, a method of ameliorating limb girdle muscular dystrophy type 2D (LGMD) in a patient is provided. In some embodiments, the method comprises the step of perfusing the vasculature of a limb of the patient with a rAAV comprising the AAV rh.74 capsid of SEQ ID NO: 2 and comprising an alpha-sarcoglycan polynucleotide (for example, the polynucleotide of SEQ ID NO: 3) in a gene expression cassette in the virus genome.

In yet another aspect, the invention provides a method of inhibiting the progression of dystrophic pathology associated with LGMD 2D. In some embodiments, the method comprises the step of perfusing the vasculature of a limb of the patient with a rAAV comprising AAV rh.74 capsid of SEQ ID NO: 2 and comprising an alpha-sarcoglycan polynucleotide (for example, the polynucleotide of SEQ ID NO: 3) in a gene expression cassette in the virus genome.

In still another aspect, a method of improving muscle function in a patient afflicted with limb girdle muscular dystrophy type 2D (LGMD 2D) is provided. In some embodiments, the method comprises the step of perfusing the vasculature of a limb of the patient with a rAAV comprising AAV rh.74 capsid of SEQ ID NO: 2 and comprising an alpha-sarcoglycan polynucleotide (for example, the polynucleotide of SEQ ID NO: 3) in a gene expression cassette in the virus genome. In some instances, the improvement in muscle function is an improvement in muscle strength. The improvement in muscle strength is determined by techniques known in the art such as the maximal voluntary isometric contraction testing (MVICT). In some instances, the improvement in muscle function is an improvement in stability in standing and walking. The improvement in stability strength is determined by techniques known in the art such as the 6-minute walk test (6MWT) or timed stair climb.

In another aspect, the invention provides a method of delivering an alpha-sarcoglycan polynucleotide to an animal (including, but not limited to, a human). In some embodiments, the method comprises the step of perfusing the vasculature of a limb of the animal with a rAAV comprising the AAV rh.74 capsid of SEQ ID NO: 2 and comprising an alpha sarcoglycan polynucleotide (for example, the polynucleotide of SEQ ID NO: 3) in a gene expression cassette in the virus genome.

Cell transduction efficiencies of the methods of the invention described above and below may be at least about 60, 65, 70, 75, 80, 85, 90 or 95 percent. In some embodiments, transduction efficiency is increased by increasing the volume of the composition in which the rAAV is delivered, pre-flushing before delivery of the rAAV and/or increasing dwell time of the rAAV.

In some embodiments of the foregoing methods of the invention, the virus genome is a self-complementary genome. In some embodiments of the methods, the genome of the rAAV lacks AAV rep and cap DNA. In some embodiments of the methods, the rAAV is AAVrh.74.tMCK.hSGCA.

In yet another aspect, the invention provides a rAAV comprising the AAV rh.74 capsid of SEQ ID NO: 2 and comprising an alpha sarcoglycan polynucleotide (for example, the polynucleotide of SEQ ID NO: 3) in a gene expression cassette in the virus genome. In some embodiments, the genome of the rAAV lacks AAV rep and cap DNA. In some embodiments, the rAAV is a self-complementary genome. In some embodiments, the rAAV is AAVrh.74.tMCK.hSGCA.

Recombinant AAV genomes of the invention comprise one or more AAV ITRs flanking a polynucleotide encoding alpha sarcoglycan. The polynucleotide is operatively linked to transcriptional control DNA, specifically promoter and polyadenylation signal DNAs that are functional in target, forming an expression cassette. AAV DNA in the rAAV genomes may be from any AAV serotype for which a recombinant virus can be derived including, but not limited to, AAV serotypes AAV-1, AAV-2, AAV-3, AAV-4, AAV-5, AAV-6, AAV-7, AAV-8, AAV-9, AAV-10 and AAV-11. As noted in the Background section above, the nucleotide sequences of the genomes of various AAV serotypes are known in the art. In some embodiments of the invention, the promoter DNAs are muscle-specific control elements, including, but not limited to, those derived from the actin and myosin gene families, such as from the myoD gene family [See Weintraub et al., *Science*, 251: 761-766 (1991)], the myocyte-specific enhancer binding factor MEF-2 [Cserjesi and Olson, *Mol. Cell. Biol.*, 11: 4854-4862 (1991)], control elements derived from the human skeletal actin gene [Muscat et al., *Mol. Cell. Biol.*, 7: 4089-4099 (1987)], the cardiac actin gene, muscle creatine kinase sequence elements [Johnson et al., *Mol. Cell. Biol.*, 9:3393-3399 (1989)] and the murine creatine kinase enhancer (MCK) element, desmin promoter, control elements derived from the skeletal fast-twitch troponin C gene, the slow-twitch cardiac troponin C gene and the slow-twitch troponin I gene: hypozia-inducible nuclear factors [Semenza et al., *Proc. Natl. Acad. Sci. USA*, 88: 5680-5684 (1991)], steroid-inducible elements and promoters including the glucocorticoid response element (GRE) [See Mader and White, *Proc. Natl. Acad. Sci. USA*, 90: 5603-5607 (1993)], and other control elements.

DNA plasmids of the invention comprise rAAV genomes of the invention. The DNA plasmids are transferred to cells permissible for infection with a helper virus of AAV (e.g., adenovirus, E1-deleted adenovirus or herpesvirus) for assembly of the rAAV genome into infectious viral particles. Techniques to produce rAAV particles, in which an AAV genome to be packaged, rep and cap genes, and helper virus functions are provided to a cell are standard in the art. Production of rAAV requires that the following components are present within a single cell (denoted herein as a packaging cell): a rAAV genome, AAV rep and cap genes separate from (i.e., not in) the rAAV genome, and helper virus functions. The AAV rep genes may be from any AAV serotype for which recombinant virus can be derived and may be from a different AAV serotype than the rAAV genome ITRs, including, but not limited to, AAV serotypes AAV-1, AAV-2, AAV-3, AAV-4, AAV-5, AAV-6, AAV-7, AAV-8, AAV-9, AAV-10 and AAV-11. Use of cognate components is specifically contemplated. Production of pseudotyped rAAV is disclosed in, for example, WO 01/83692 which is incorporated by reference herein in its entirety.

A method of generating a packaging cell is to create a cell line that stably expresses all the necessary components for AAV particle production. For example, a plasmid (or multiple plasmids) comprising a rAAV genome lacking AAV rep and cap genes, AAV rep and cap genes separate from the rAAV genome, and a selectable marker, such as a neomycin resistance gene, are integrated into the genome of a cell. AAV genomes have been introduced into bacterial plasmids by procedures such as GC tailing (Samulski et al., 1982, Proc. Natl. Acad. S6. USA, 79:2077-2081), addition of synthetic linkers containing restriction endonuclease cleavage sites (Laughlin et al., 1983, Gene, 23:65-73) or by direct, blunt-end ligation (Senapathy & Carter, 1984, J. Biol. Chem., 259:4661-4666). The packaging cell line is then infected with a helper virus such as adenovirus. The advantages of this method are that the cells are selectable and are suitable for large-scale production of rAAV. Other examples of suitable methods employ adenovirus or baculovirus rather than plasmids to introduce rAAV genomes and/or rep and cap genes into packaging cells.

General principles of rAAV production are reviewed in, for example, Carter, 1992, Current Opinions in Biotechnology, 1533-539; and Muzyczka, 1992, Curr. Topics in Microbial. and Immunol., 158:97-129). Various approaches are described in Ratschin et al., Mol. Cell. Biol. 4:2072 (1984); Hermonat et al., Proc. Natl. Acad. Sci. USA, 81:6466 (1984); Tratschin et al., Mol. Cell. Biol. 5:3251 (1985); McLaughlin et al., J. Virol., 62:1963 (1988); and Lebkowski et al., 1988 Mol. Cell. Biol., 7:349 (1988). Samulski et al. (1989, J. Virol., 63:3822-3828); U.S. Pat. No. 5,173,414; WO 95/13365 and corresponding U.S. Pat. No. 5,658,776; WO 95/13392; WO 96/17947; PCT/US98/18600; WO 97/09441 (PCT/US96/14423); WO 97/08298 (PCT/US96/13872); WO 97/21825 (PCT/US96/20777); WO 97/06243 (PCT/FR96/01064); WO 99/11764; Perrin et al. (1995) Vaccine 13:1244-1250; Paul et al. (1993) Human Gene Therapy 4:609-615; Clark et al. (1996) Gene Therapy 3:1124-1132; U.S. Pat. No. 5,786,211; U.S. Pat. No. 5,871,982; and U.S. Pat. No. 6,258,595. The foregoing documents are hereby incorporated by reference in their entirety herein, with particular emphasis on those sections of the documents relating to rAAV production.

The invention thus provides packaging cells that produce infectious rAAV. In one embodiment packaging cells may be stably transformed cancer cells such as HeLa cells, 293 cells and PerC.6 cells (a cognate 293 line). In another embodiment, packaging cells are cells that are not transformed cancer cells, such as low passage 293 cells (human fetal kidney cells transformed with E1 of adenovirus), MRC-5 cells (human fetal fibroblasts), WI-38 cells (human fetal fibroblasts), Vero cells (monkey kidney cells) and FRhL-2 cells (rhesus fetal lung cells).

The rAAV may be purified by methods standard in the art such as by column chromatography or cesium chloride gradients. Methods for purifying rAAV vectors from helper virus are known in the art and include methods disclosed in, for example, Clark et al., Hum. Gene Ther., 10(6): 1031-1039 (1999); Schenpp and Clark, Methods Mol. Med., 69 427-443 (2002); U.S. Pat. No. 6,566,118 and WO 98/09657.

In another embodiment, the invention contemplates compositions comprising rAAV of the present invention. Compositions of the invention comprise rAAV in a pharmaceutically acceptable carrier. The compositions may also comprise other ingredients such as diluents. Acceptable carriers and diluents are nontoxic to recipients and are preferably inert at the dosages and concentrations employed, and include buffers such as phosphate, citrate, or other organic acids; antioxidants such as ascorbic acid; low molecular weight polypeptides; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as Tween, pluronics or polyethylene glycol (PEG).

Titers of rAAV to be administered in methods of the invention will vary depending, for example, on the particular rAAV, the mode of administration, the treatment goal, the individual, and the cell type(s) being targeted, and may be determined by methods standard in the art. Titers of rAAV may range from about $1 \times 10^6$, about $1 \times 10^7$, about $1 \times 10^8$, about $1 \times 10^9$, about $1 \times 10^{10}$, about $1 \times 10^{11}$, about $1 \times 10^{12}$, about $1 \times 10^{13}$ to about $1 \times 10^{14}$ or more DNase resistant particles (DRP) per ml. Dosages may also be expressed in units of viral genomes (vg) (i.e., $1 \times 10^7$ vg, $1 \times 10^8$ vg, $1 \times 10^9$ vg, $1 \times 10^{10}$ vg, $1 \times 10^{11}$ vg, $1 \times 10^{12}$ vg, $1 \times 10^{13}$ vg, $1 \times 10^{14}$ vg, respectively).

Methods of transducing a target cell (e.g., a skeletal muscle, smooth muscle or cardiac muscle cell) with rAAV, in vivo or in vitro, are contemplated by the invention. The methods comprise the step of administering an effective dose, or effective multiple doses, of a composition comprising a rAAV of the invention to an animal (including a human being) in need thereof. If the dose is administered prior to development of a LGMD2D, the administration is prophylactic. If the dose is administered after the development of LGMD2D, the administration is therapeutic. In embodiments of the invention, an effective dose is a dose that alleviates (eliminates or reduces) at least one symptom associated with LGMD2D being treated, that slows or prevents progression to LGMD2D, that slows or prevents progression of a disorder/disease state, that diminishes the extent of disease, that results in remission (partial or total) of disease, and/or that prolongs survival.

Combination therapies are also contemplated by the invention. Combination as used herein includes simultaneous treatment or sequential treatments. Combinations of methods of the invention with standard medical treatments (e.g., corticosteroids and/or immunosuppressive drugs) are specifically contemplated, as are combinations with novel therapies.

Sterile injectable solutions are prepared by incorporating rAAV in the required amount in the appropriate solvent with various other ingredients enumerated above, as required, followed by filter sterilization. Generally, dispersions are prepared by incorporating the sterilized active ingredient into a sterile vehicle which contains the basic dispersion medium and the required other ingredients from those enumerated above. In the case of sterile powders for the preparation of sterile injectable solutions, the preferred methods of preparation are vacuum drying and the freeze drying technique that yield a powder of the active ingredient plus any additional desired ingredient from the previously sterile-filtered solution thereof.

The composition comprising a rAAV of the invention may also be administered to an animal (including a human being) in need thereof using a system such as is illustrated in FIG. 5, and/or according to a method such as illustrated in FIG. 6. In this regard, FIGS. 7 and 8 may have been simplified by the omission of selected elements for the purpose of more clearly showing other elements. Such omissions of elements in some figures are not necessarily indicative of the presence or absence of particular elements in any of the exemplary embodiments, except as may be explicitly delineated in the corresponding written description. FIG. 5 is not necessarily to scale.

FIG. 5 illustrates an exemplary system 100 that may be used according to the present disclosure to deliver the rAAV, potentially in combination with other treatments and therapies, according to an isolated whole limb recirculation protocol. The system 100 includes a venous catheter 102, a pump 104, an optional oxygenator 106, an optional heat exchanger 108 (which may according to certain embodiments be formed integrally with the oxygenator 106), and an arterial catheter 110. In addition, the system 100 may include a one or more sets defining a circuit 120 connecting the venous catheter 102 to the arterial catheter 110, and received within or connected to the pump 104, the oxygenator 106, and the heat exchanger 108. These sets may include one or more connectors, which may be luer-type connectors, as well as tubing and reservoirs.

In fact, according to one embodiment of the present circuit 120, the circuit 120 may include a first connection (and collection) site 122 and a second connection (and introduction) site 124. Either or both of the connection sites 122, 124 may be defined by a luer connector incorporating a stopcock, permitting fluid to be diverted from the circuit 120. For example, the first connection site 122 may include first and second luer connectors, each with a stopcock and attached line. The second connection site 124 may include a single stopcock with attached line. The lines running between the catheters 102, 110, the other equipment (pump 104, optional oxygenator 106, optional heat exchanger 108) and the sites 122, 124 may be exaggerated in FIG. 5 for ease of illustration.

As illustrated, the venous catheter 102 is connected to a first end of the circuit 120 that is received in the pump 104, which may be a peristaltic or roller pump according to certain embodiments. The circuit 120 may also be connected to the oxygenator 106 if the perfusate passing through the circuit 120 is blood, for example. If fluids other than blood are passed through the circuit 120 between the catheters 102, 110, then the oxygenator 106 may not be required. Additionally, the circuit 120 may be received or connected to a heat exchanger 108, which heat exchanger 108 may be used to control or maintain the temperature of the fluid passing through the circuit 120. As noted above, the heat exchanger 108 is presently believed to be optional, and may not be included in all embodiments of the present disclosure. The circuit 120 is connected at a second end to the arterial catheter 110.

The system 100 may be connected to a patient 150, and in particular, to a limb 152 (e.g., lower extremity) of the patient 150 that has been isolated from the remainder of the patient's body 154 by a tight or tightly-placed tourniquet 156, which is provided as an exemplary isolation device or system. The venous catheter 102 may be placed or disposed within a vein 160 (e.g., femoral vein) of the limb 152, while the arterial catheter 110 may be placed or disposed within an artery 162 (e.g., femoral artery) of the limb 152. As illustrated, the insertion site of the venous catheter 102 and the insertion site of the arterial catheter 110 are adjacent each other and only slightly distal of the tourniquet 156.

Where the limb 152 is the lower extremity (i.e., a leg), both catheter sites may be in the groin region. However, according to other embodiments, the venous catheter 102 may be disposed only slightly distal to the tourniquet 156, while the arterial catheter 110 is disposed at a considerable distance from the tourniquet 156. For example, where the limb 152 is a leg, one site may be in the groin, and the other at the ankle. According to still other embodiments, an upper extremity (i.e., an arm) may be targeted.

The catheters 102, 110 may be introduced into the vein and artery, respectively, either by surgical cut down and blunt dissection or by less invasive procedures, such as the Seldinger technique (percutaneously). In regard to the later technique, it may be possible to introduce the catheters at a location remote to the limb undergoing perfusion and to advance the catheters from the remote site to a location proximate to the limb to be perfused. In fact, balloon catheters may be used to perform both the connection to the circuit 120 and (when inflated) the isolation of the limb from the remainder the patient's body.

The system 100 is operated to circulate a fluid, which may be referred to as the perfusate, from the point of insertion of the arterial catheter 110 through the limb 152 to the point of insertion of the venous catheter 110, through the pump 104, optional oxygenator 106, and optional heat exchanger 108, and back to the arterial catheter 110. As noted above, certain embodiments may employ the patient's blood, potentially in combination with additional blood or blood components. However, according to certain embodiments of the present disclosure, the perfusate may be saline or a buffer solution. According to a non-blood perfusate embodiment, the blood may be removed from the limb 152 via the venous catheter 102 (and the site 122), while the perfusate is introduced via the arterial catheter 110 (and the site 124).

The system 100 may also include sensors that may be used to monitor the flow of the perfusate through the system 100 and the limb 152, and may even be used to control the operation of the pump 104, for example. In particular, pressure sensors 170, 172 may be disposed upstream (venous side) and downstream (arterial side) of the pump 104 and optional oxygenator 106 and heat exchanger 108. In particular, the sensor 170 may be used to determine if a low pressure condition is occurring on upstream of the pump 104 such that the operation of the pump 104 should be stopped momentarily to prevent damage to the blood vessels of the limb 152.

A method 200 of operating the system 100 is illustrated in FIG. 6 to deliver an rAAV. It will be understood that the method 200 may be carried out using equipment other than that illustrated in FIG. 5 (i.e., system 100). In addition, it will be understood that the system 100 may be used to carry out a method other than the method 200 illustrated in FIG. 6. However, according to certain embodiments, the system 100 may be operated in accordance with the method 200.

The method 200 begins at block 202 with the insertion of the catheters 102, 110, or at least with the insertion of the venous catheter 102 into the vein 160. At block 202, the circuit 120 may also be connected to the catheters 102, 110 (and thereby to the vasculature of the limb 152). Method 200 continues at block 204 with the isolation of the limb 152 from the remainder 154 of the body, which may be achieved by applying the tourniquet 156 to the limb 152 for example. It will be recognized that the order of the steps of blocks 202 and 204 may in fact be reversed according to certain embodiments of the present method. Depending on the choice of perfusate, the method 200 may then proceed to optional block 206.

If the perfusate is other than blood (i.e., a non-blood perfusate), then at block 206 a volume of the patient's blood is removed from the limb 152 via the venous catheter 102 and the site 122 while the non-blood perfusate (e.g., a buffer solution, such as Normosol-R available from Hospira Inc., Lake Forest, Ill.) is introduced into the circuit 120 and the limb 152 via the site 124 and the arterial catheter 110. The blood may be disposed in a sterile blood bag, and an anti-coagulant may be added to the blood, such as ACD-A or Heparin, for storage. The volume of blood would then be stored using conventional methods for later reintroduction, as explained in detail below.

Alternatively, the patient's own blood may be used as the perfusate. However, if the patient's own blood is used, then it may be advisable to provide for oxygenation of the blood by way of the optional oxygenator 106. Moreover, it may also be advisable to screen the blood for antibodies and complements that have specific binding sites for the rAAV, or that exhibit non-specific biding with the rAAV. If the patient is naïve to the rAAV, no further action may be required. However, if the patient has antibodies or complements that exhibit specific or non-specific binding with the rAAV, the blood may need to be filtered before it is used as the perfusate in the method 200. For example, plasmapheresis may be used to remove the antibodies and/or complements from the patient's blood.

In either event, some additional perfusate may be added to facilitate the travel of the rAAV within the limb 152, and in particular within the muscles of the limb 152. However, because vascular pressures that are excessive are believed to be detrimental to the tissue of the limb 152, overall volume of perfusate used is minimized according to certain embodiments of the present disclosure.

Once the step of block 206 has been performed, if required, the pump 104 is activated to cause the perfusate to circulate through the limb 152 to perfuse limb 152 at block 208. According to certain embodiments of the present disclosure, after perfusion of the limb 152 has begun, the rAAV may be administered at block 210 through its introduction (injection) into the circuit 120 and the limb 152, for example via the arterial catheter 110. According to other embodiments, the administration of the rAAV may occur prior to the activation of the pump 104 or may be delayed some period of time after the perfusion has begun. The rAAV is then permitted to recirculate, or pass repeatedly, with the perfusate through the circuit 120 and limb 152 for a period of time at block 212.

The period of time that the perfusate and rAAV is recirculating may be varied from patient to patient, and between treatments of the same patient. For example, the time period may be at least 1, 2, 3, 4, 5, 6, 7, 8, 9, or 10 minutes. For that matter, the time period may be at least 10 minutes, 20 minutes, 30 minutes, 40 minutes, 50 minutes or 1 hour. According to certain embodiments, the time period may even exceed 3 hours, although many treatments may be less than 2 hours in length. According to particular embodiments, the time period may be approximately or about 30 minutes.

Once the recirculation of the perfusate and rAAV has been conducted over the desired time period, the perfusate and any rAAV remaining in the perfusate may be removed from the circuit 120 and the limb 152 at block 214. While it may be possible to perform a flush of the limb 152 by introducing a perfusate without rAAV as the perfusate with residual rAAV is removed, it is not expected that such a flush will be routinely performed. It also may be possible to reintroduce or reperfuse the limb 152 at this point with the volume of the patient's blood removed from the limb 152 at the beginning of the procedure, although this also may not occur according to all embodiments of the present method 200.

Once the perfusate has been replaced with the blood at block 214 (if desired), the isolation of the limb 152 may be discontinued, by removing the tourniquet 156 for example, at block 216. At this point or immediately prior to block 216, the catheters 102, 110 may be removed from the vein 160 and artery 162 of the limb 152 at block 218, thereby disconnecting the circuit 120 from the limb 152.

It is believed that the use of a recirculating system, such as the system 100, and a method of recirculation, such as the method 200, may have one or more advantages with regard to the administration of the rAAV. To begin, the recirculation thus described facilitates the travel of the rAAV to all or nearly all regions of the limb 152, and in particular to all or nearly all of the muscle fibers of the muscles of the limb 152, and for those regions to be exposed to the rAAV multiple times. Both the widespread nature of the exposure, as well as the duration/frequency of the exposure, are believed to assist in the rAAV transferring the genetic material into the muscle cells and the interstitial spaces between the muscle fiber cells of the targeted limb 152. However, further advantages may be obtained when a non-oxygenated perfusate is used in the system 100 and the limb 152. It will be recognized that if a non-oxygenated perfusate (e.g., a buffer solution) is used in the system 100 and limb 152, the tissue of the limb will experience hypoxia and/or acidosis over time because of the lack of oxygen in the circulating perfusate. Hypoxia and acidosis are known to cause blood vessels to dilate (vasodilatation). As a consequence, it is believed that the travel of the perfusate and the rAAV carried by the perfusate will be further facilitated because of the dilated nature of the vessels, permitting the perfusate and rAAV to travel deep within the tissues of the targeted limb 152.

BRIEF DESCRIPTION OF THE DRAWING

FIG. 1 is an alignment of the AAV rh.74 (SEQ ID NO: 2) and AAV8 capsid (SEQ ID NO: 4) amino acid sequences.

FIG. 4 is the rh74 genome sequence (SEQ ID NO: 5) wherein nucleotides 210-2147 are the Rep 78 gene open reading frame, 882-208 are the Rep52 open reading frame, 2079-2081 are the Rep78 stop, 2145-2147 are the Rep78 stop, 1797-1800 are a splice donor site, 2094-2097 are a splice acceptor site, 2121-2124 are a splice acceptor site, 174-181 are the p5 promoter +1 predicted, 145-151 are the p5 TATA box, 758-761 are the p19 promoter +1 predicted, 732-738 are the p19 TATA box, 1711-1716 are the p40 TATA box, 2098-4314 are the VP1 Cap gene open reading frame, 2509-2511 are the VP2 start, 2707-2709 are the VP3 start and 4328-4333 are a polyA signal.

FIG. 7 shows the average transgene expression throughout the lower extremity following vascular delivery and recirculation of $6\times10^{12}$ vg/kg of rAAV comprising an enhanced green fluorescent protein (eGFP) transgene, AAVrh.74.CMD.eGFP. A) Each representative panel is a direct fluorescent image of a section of muscle demonstrating the extent of eGFP expression. The Biceps (a non-targeted muscle from the upper extremity is presented as a negative control). B) Each bar represents an average of two muscles—one from each lower extremity of a Rhesus macaque and shows the percent muscle fiber transgene expression of the major lower extremity muscles. QVL=Vastus Lateralis, QRF=Rectus Femoris, QVM=Vastus Medialis, QVI=Vastus Intermedius, HBF=Biceps Femoris, HSM=Semimembranosus, HST=Semitendinosus, HSart=Sartorius, HGrac=Gracilis, GlutMax=Gluteus Max, GlutMed=Gluteus Med, TA=Tibialis Anterior, EDL=Extensor Digitorum Longus, MG=Medial Gastrocnemius, LG=Lateral Gastrocnemius, Sol=Soleus.

FIG. 8 shows the average transgene expression throughout the lower extremity following vascular delivery and recirculation of $2\times10^{12}$ vg/kg of vector (AAVrh.74.CMD.eGFP). A) Each representative panel is a direct fluorescent image of a section of muscle demonstrating the extent of transgene expression. The Biceps (a non-targeted muscle from the upper extremity is presented as a negative control). B) Each bar represents an average of two muscles—one from each lower extremity of a Rhesus macaque and shows the percent muscle fiber transgene expression of the major lower extremity muscles. QVL=Vastus Lateralis, QRF=Rectus Femoris, QVM=Vastus Medialis, QVI=Vastus Intermedius, HBF=Biceps Femoris, HSM=Semimembranosus, HST=Semitendinosus, HSart=Sartorius, HGrac=Gracilis, GlutMax=Gluteus Max, GlutMed=Gluteus Med, TA=Tibialis Anterior, EDL=Extensor Digitorum Longus, MG=Medial Gastrocnemius, LG=Lateral Gastrocnemius, Sol=Soleus.

FIG. 9 shows the average transgene expression throughout the lower extremity following vascular delivery and recirculation of $6\times10^{12}$ vg/kg of AAVrh.74.MCK.microdystrophin. A) Each representative panel is an immunofluorescent image of a section of muscle demonstrating the extent of transgene expression. The Biceps (a non-targeted muscle from the upper extremity is presented as a negative control). B) Each bar represents an average of two muscles—one from each lower extremity of a Rhesus macaque and shows the percent muscle fiber transgene expression of the major lower extremity muscles. QVL=Vastus Lateralis, QRF=Rectus Femoris, QVM=Vastus Medialis, QVI=Vastus Intermedius, HBF=Biceps Femoris, HSM=Semimembranosus, HST=Semitendinosus, HSart=Sartorius, HGrac=Gracilis, GlutMax=Gluteus Max, GlutMed=Gluteus Med, LCF=Lateral Caudal Femoris, TA=Tibialis Anterior, EDL=Extensor Digitorum Longus, MG=Medial Gastrocnemius, LG=Lateral Gastrocnemius, Sol=Soleus.

FIG. 10 shows the average transgene expression throughout the lower extremity following vascular delivery and recirculation of $6\times10^{12}$ vg/kg of AAVrh.74.tMCK.SGCA. A) Each representative panel is an immunofluorescent image of a section of muscle demonstrating the extent of transgene expression. The Biceps (a non-targeted muscle from the upper extremity is presented as a negative control). B) Each bar represents the average of two muscles—one from each lower extremity of a Rhesus macaque and shows the percent muscle fiber transgene expression of the major lower extremity muscles. QVL=Vastus Lateralis, QRF=Rectus Femoris, QVM=Vastus Medialis, QVI=Vastus Intermedius, HBF=Biceps Femoris, HSM=Semimembranosus, HST=Semitendinosus, HSart=Sartorius, HGrac=Gracilis, GlutMax=Gluteus Max, GlutMed=Gluteus Med, LCF=Lateral Caudal Femoris, TA=Tibialis Anterior, EDL=Extensor Digitorum Longus, MG=Medial Gastrocnemius, LG=Lateral Gastrocnemius, Sol=Soleus.

EXAMPLES

Figure 2:
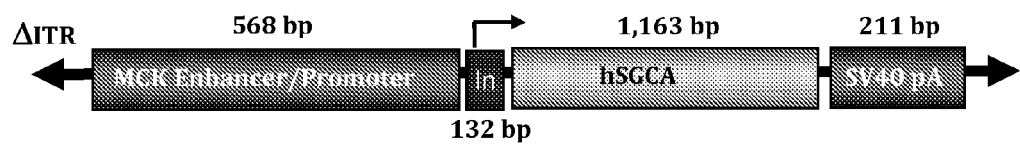
FIG. 2 shows the tMCK-aSG gene cassette.

Thus, aspects and embodiments of the invention are illustrated by the following examples. Example 1 describes the isolation of AAV rh.74. Example 2 describes alpha-sarcoglycan gene expression from a highly active expression cassette combined with a self-complementary AAV vector. Example 3 describes gene delivery via the mouse vasculature using AAV rh.74. Example 4 describes the vascular delivery of AAVrh.74.tMCK.hSGCA in non-human primates. Example 5 describes the biodistribution of the AAVrh.74.tMCK.hSGCA vector in the macaques. Example 6 describes administration of AAVrh.74.tMCK.hSGCA to a human patient. Example 7 describes isolated whole limb re-circulation (IWRLC) methodology according to the invention. Example 8 describes IWLRC in the non-human primate with a reporter construct. Example 9 describes IWLRC in the non-human primate with therapeutic transgenes. Example 10 describes vascular delivery of SC rAAV8.tMCK.hSGCA to alpha-sarcoglycan knock-out mice.

Example 1

Isolation of AAV rh.74

A unique AAV serotype was isolated from a rhesus macaque lymph node using a novel technique termed Linear Rolling Circle Amplification. Using the LRCA process, double-stranded circular AAV genomes were amplified from several rhesus macaques. The method is predicated on the ability to amplify circular AAV genomes by isothermic rolling circle amplification using phi29 phage DNA polymerase and AAV specific primers. LRCA products are contiguous head-to-tail arrays of the circular AAV genomes from which full-length AAV Rep-Cap molecular clones were isolated. Four isolates were sequenced and the predicted amino acid sequences for Rep and Cap ORFs were aligned and compared to previously published serotypes (Table). VP1 protein sequences were analyzed and revealed homology to the NHP AAV clades D, E, and AAV 4-like virus isolates. Analysis of the Rep78 (top portion of Table) ORF revealed strong homology to AAV 1 (98-99%).

TABLE 1

| | AAV 1 | AAV 4 | AAV 7 | AAV 8 | rh.73 | rh.74 | rh.75 | rh.76 |
|---|---|---|---|---|---|---|---|---|
| AAV 1 | | 90 | 98 | 95 | 98 | 98 | 99 | |
| AAV 4 | 63 | | 90 | 87 | 90 | 90 | 90 | |
| AAV 7 | 85 | 63 | | 96 | 97 | 98 | 98 | |
| AAV 8 | 84 | 63 | 88 | | 97 | 97 | 95 | |
| rh.73 | 79 | 61 | 83 | 80 | | 99 | 99 | |
| rh.74 | 84 | 63 | 88 | 93 | 80 | | 99 | |
| rh.75 | 65 | 82 | 82 | 64 | 62 | 64 | | |
| rh.76 | 85 | 63 | 91 | 86 | 84 | 86 | 84 | |

Similarity of published AAV sequences and the new AAV sequences determined using one-pair alignment according to the Lipman-Pearson method implemented in the MegAlgn software in DNASTAR (DNASTAR Inc.) Light faced numbers (top, right) represent similarity in Rep78 sequences, whereas bold-faced numbers (lower, left) represent similarity in VP1 capsid sequences.

One macaque tissue sample (rh426-M) yielded a divergent AAV8-like isolate termed rh.74 that shares 93% sequence identity with AAV8. The nucleotide and amino acid sequences of the rh.74 capsid gene are respectively set out in SEQ ID NOs: 1 and 2. FIG. 1 shows an alignment of the rh.74 (SEQ ID NO: 2) and the AAV8 capsid (SEQ ID NO: 4) amino acid sequences.

The rh.74 capsid gene sequence was cloned into an AAV helper plasmid containing the Rep gene from AAV2 to provide vector replication functions for recombinant AAV vector production.

Example 2

Robust Alpha-Sarcoglycan Gene Expression Using a Highly Active Expression Cassette Combined with a Self-Complementary AAV Vector A vector was designed with several features to maximize the opportunity for clinical success. First, to ameliorate possible immune responses to the vector expression cassette, a synthetic codon-optimized human alpha-sarcoglycan cDNA (hSCGA) was placed under the control of a muscle specific promoter (the truncated muscle creatine kinase promoter/enhancer). The tMCK promoter was a gift from Dr. Xiao Xiao (University of North Carolina). It is a modification of the previously described CK6 promoter [Shield et al., Mol Cell Biol, 16:5058-5068 (1996)] and includes a modification in the enhancer upstream of the promoter region containing transcription factor binding sites. The enhancer is composed of two E-boxes (right and left). The tMCK promoter modification includes a mutation converting the left E-box to a right E-box (2R modification) and a 6 bp insertion (S5 modification). The nucleotide sequence of the hSCGA is set out in SEQ ID NO: 3. Second, the construct also includes a chimeric intron to promote high level expression. The chimeric intron is composed of the 5' donor site from the first intron of the human β-globin gene and the branchpoint and 3' splice acceptor site from the intron that is between the leader and the body of an immunoglobulin gene heavy chain variable region. Third, a synthetic SV40 polyadenylation signal is used for efficient transcription termination. A schematic of the expression cassette is shown below in FIG. 2.

Figure 3:
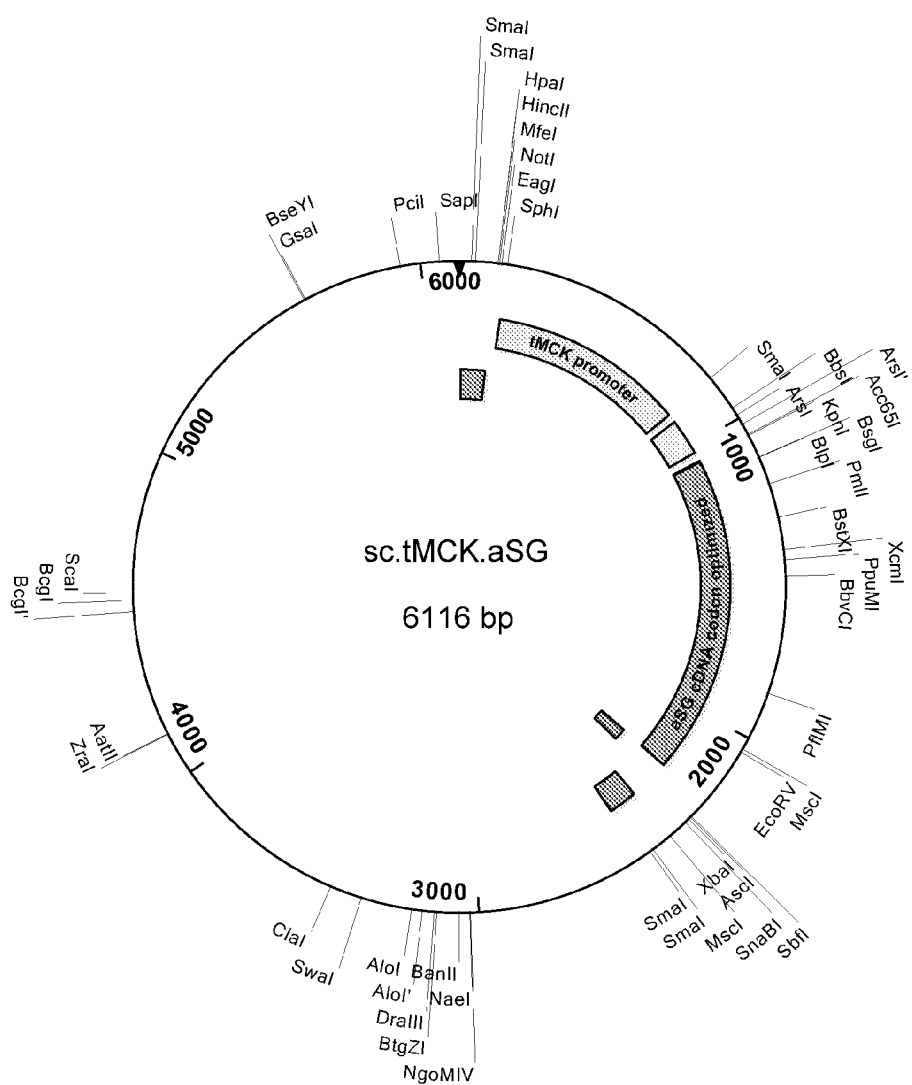
FIG. 3 shows the sc.tMCk.aSG vector plasmid.
Figure 5:
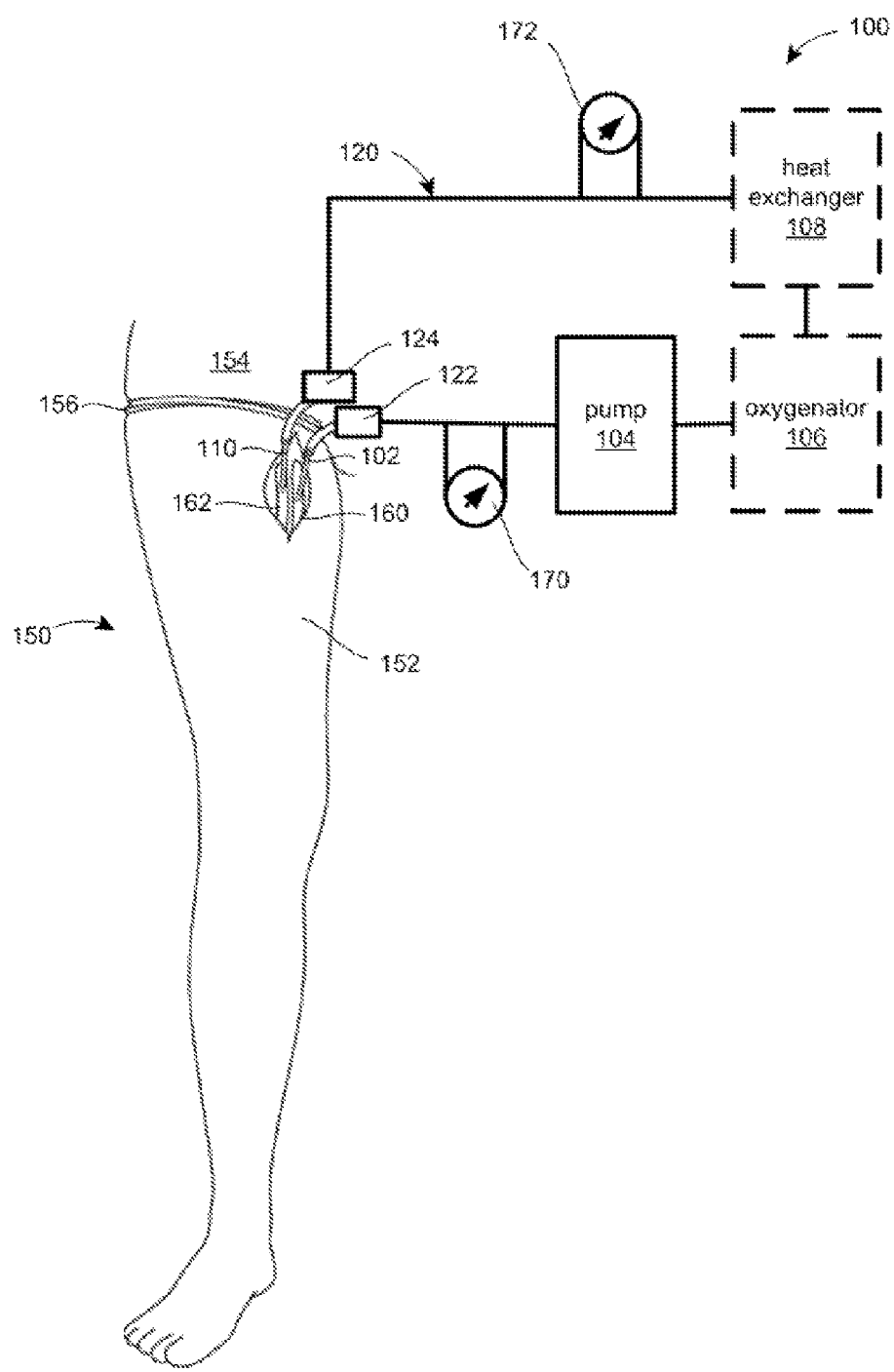
FIG. 5 is a schematic illustration of a system for recirculating the rAAV according to the present disclosure.

The expression cassette was inserted into the pHpa7 self-complementary AAV vector plasmid backbone to generate plasmid sc.tMCK.aSG shown in FIG. 3. The location of the expression cassette elements in the plasmid is given in Table 2 below.

TABLE 2

| Type | Start | End | Name | Description |
|---|---|---|---|---|
| REGION | 1 | 116 | ITR | Inverted terminal repeat |
| REGION | 147 | 860 | tMCKp | Truncated MCK promoter |
| REGION | 891 | 1024 | sd/sa | Chimeric intron |
| GENE | 1064 | 2228 | ha-SG | Human alpha sarcoglycan gene |
| REGION | 2229 | 2280 | pA | SV40 late polyadenylation signal |
| REGION | 2377 | 2480 | ITR | Inverted terminal repeat |

To maximize vector potency and reduce the dosing requirements, a self-complementary (SC) AAV vector was produced. SC AAV vectors demonstrate increased gene expression and express the protein product sooner than standard single-stranded AAV vectors. This improvement is achieved by deleting a small portion of one AAV inverted terminal repeat (ITR) that causes AAV replication to proceed to a dimeric replication intermediate that is then packaged into AAV particles.

The recombinant SC AAV vector (AAVrh.74.tMCK.hSGCA) expressing the alpha-sarcoglycan gene from the muscle specific tMCK promoter was produced by a modified cross-packaging approach using the plasmid sc.tMCK.aSG in an adenovirus-free, triple plasmid DNA transfection (CaPO$_4$ precipitation) method in HEK293 cells [Rabinowitz et al., *J. Virol.*, 76:791-801 (2002)]. Vector was produced by co-transfecting with an AAV helper plasmid rep2-cap rh.74 and an adenovirus helper plasmid in similar fashion as that previously described [Wang et al., *Gene. Ther.*, 10:1528-1534 (2003)]. Plasmid rep2-cap rh.74 encodes the wild-type AAV2 rep gene and rh.74 cap gene, and the adenovirus helper plasmid (pAdhelper) expresses the adenovirus type 5 E2A, E4ORF6, and VA I/II RNA genes which are required for high-titer rAAV production.

Vectors were purified from clarified 293 cell lysates by sequential iodixanol gradient purification and anion-exchange column chromatography using a linear NaCl salt gradient as previously described [Clark et al., *Hum. Gene Ther*, 10:1031-1039 (1999)]. Vector genome (vg) titers were measured using QPCR based detection with a tMCK specific primer/probe set and utilized the Prism 7500 Taqman detector system (PE Applied Biosystems) as previously described (Clark et al., supra). Vector stock titers ranged between 1-10×10$^{12}$ vg/mL.

Example 3

Efficient Gene Delivery via the Mouse Vasculature Using AAV rh.74

With respect to clinical application, rather than delivering alpha-sarcoglycan gene by direct injection into the muscle, meaningful results will be best attained using a gene transfer approach that has the ability to reach widespread muscle targets resulting in an improvement in the patient's quality of life. A vascular delivery approach allows for a one-time vector infusion to reach multiple muscles instead of direct injections that would be necessary using a direct injection intramuscular approach. Moreover, benefits of a regional vascular approach include: lack of widespread dissemination of virus; safe passage of the virus directly to the targeted muscles; and transduction of multiple muscles in, for example, the leg.

AAVrh.74 Micro-Dystrophin Gene Delivery Versus AAV1 and AAV6 Delivery

The AAV1 serotype transduces muscle efficiently by direct intramuscular injection, however comparative studies demonstrated that AAVrh.74 delivered through the circulation is vastly superior to AAV1 and superior to AAV6 in transducing skeletal muscle via this route. As described in Rodino-Klapac et al., *J. of Transl. Med*, 5: 45 (2007), AAV6 and AAV rh.74 carrying a micro-dystrophin gene demonstrated ease in crossing the vascular barrier when delivered to skeletal muscle in the mdx mouse through a catheter in the femoral artery. Extremely efficient regional vascular delivery was observed using AAVrh.74.micro-dystrophin, and yielded percent transduced myofibers as follows: 94.5±0.9 (1 month), 91.3±3.1 (2 months), and 89.6±1.6% (3 months). AAV6.micro-dystrophin treated animals demonstrated 87.7±6.8 (1 month), 78.9±7.4 (2 months), and 81.2±6.2% (3 months) transduction. In striking contrast, AAV1 demonstrated very low transduction efficiency [0.9±0.3 (1 month), 2.1±0.8 (2 months), and 2.1±0.7% (3 months)] by the vascular delivery route. The delivery of micro-dystrophin through the femoral artery was accompanied by functional improvement as measured by protection against contraction-induced injury and improvement in tetanic force.

AAVrh.74.tMCK.hSGCA Vascular Delivery in Knock-Out Mice

In the present experiments, the AAVrh.74.tMCK.hSGCA was delivered by isolated limb perfusion to the alpha-sarcoglycan knock-out mouse.

Sedated and anesthetized animals secured to a surgical platform were prepared and draped in the usual sterile fashion. Suture-tourniquets (3.0 braided silk) were placed loosely around the thigh near the inguinal region. A small incision was placed over the femoral bundle visible through the skin. The femoral artery was isolated and cannulated with a heat-pulled polyethylene (PE) 10 catheter prefilled with normal saline and secured in place. The tourniquet was tightened and a pre-flush of normal saline was delivered. Following the pre-flush, the vector dose 2×10$^{12}$ vg/kg wt was administered and allowed to dwell for 10 minutes. After the 10-minute dwell a final post-flush of normal saline was delivered, and the catheter and tourniquet removed and the animal recovered.

Three-months post-gene transfer, transduction levels were observed averaging 78.2±11% of muscle fibers. Not only was the transgene appropriately expressed at the muscle fiber periphery in greater than 75% of muscle fibers, muscle function (measured as specific force) was restored in treated animal muscles compared to non-treated muscle. In other experiments, gene transfer of up to 90% positive fibers in the lower extremity musculature was observed.

Example 4

AAVrh.74.tMCK.hSGCA Vascular Delivery in Non-Human Primates

The above success in the mouse promulgated extensive studies in non-human primates using both cynomologus and rhesus macaques. In both species, a clinically relevant, intra-arterial delivery system was used.

Sedated and anesthetized animals were secured to a surgical bed. Proximal and distal tourniquets were loosely positioned above the knee and below the gastrocemius muscle of a macaque. A small incision was placed at the femoral triangle and the femoral artery was identified and dissected free and looped with proximal and distal ligatures to control bleeding and facilitate catheter introduction. The femoral artery was cannulated with a 3.0 Fr introducer sheath via a modified Seldinger method by passing the pre-flushed sheath over a wire previously placed in the artery. The sheath was advanced only a few centimeters and secured in place with a 3.0 braided silk suture.

Heparinization was achieved with 50 U/kg body weight via the sheath and the sheath was cleared with normal saline. Fluoroscopy was used to generate a road map of the vasculature by administering a few milliliters of contrast agent through the sheath and capturing the fluoroscopic image. A 3.0 Fr, 50 cm long catheter was placed into the introducer sheath and advanced a few centimeters. A guide wire (0.018 in., diameter) was placed through the catheter and, under fluoroscopic guidance, advanced to the sural arteries, which perfuse the two heads of the gastrocnemius. Once the catheter was correctly positioned, the vascular bed of the gastrocnemius was isolated by the placement of proximal and distal tourniquets. The proximal tourniquet was placed above the knee and just proximal to the catheter tip. Optimal placement of the proximal tourniquet was assessed by partial tourniquet tightening and visualization of a small volume (few milliliters) of injected contrast agent. Once the relationship of the proximal tourniquet to catheter tip was established, the contrast was flushed from the limb with normal saline and the distal tourniquet was positioned just below the gastrocnemius. The second tourniquet provides compartmentalization of the gastrocnemius. Dosing began with a pre-flush volume (2.5 mL/kg) of normal saline delivered over 60 sec. with the tourniquets pulled snug. While the final volume was administered, the tourniquets were pulled tight to occlude blood flow. With the tourniquets pulled tight the rAAV vector carrying the gene of interest, AAVrh.74.tMCK.hSGCA ($2\times10^{12}$ viral genomes per kg in 2.5 mL per kg volume), was administered over 60 s. Allow 10 min. dwell time with the tourniquets left tight. Following the 10 min dwell and with the tourniquets still tight and occluding blood flow, a post-volume of normal saline (2.5 mL/kg) was administered over 60 s. At the completion of dosing the tourniquets and catheter were removed and direct pressure was applied to the wound for 10 min to control bleeding. The wound was closed with a continuous subcuticular 4.0 Vicryl suture. A pressure dressing was applied to the site and kept in place until the animal awoke from anesthesia.

Following the above vector delivery protocol, similarly treated animals were sacrificed 12 to 24 weeks later and muscle samples were removed for storage and study. Gene expression was measured by antibody staining of the transgene expression product in situ.

Muscle transduction exceeded 75% in the muscles of interest using doses applicable to a clinical trial. Evaluation of antibody stained microscopic images of the treated muscles showed that micro-dystrophin, alpha-sarcoglycan or a FLAG-tag (6 amino acid tag attached to the transgene) was expressed at the fiber periphery, the region known as the sarcolemma. This is the region of normal expression for these proteins. Muscles not targeted had very low levels of transgene expression highlighting the specific nature of the targeting. Robust expression in other animals treated was observed for up to six months.

Example 5

AAVrh.74 Vector Biodistribution

Figure 6:
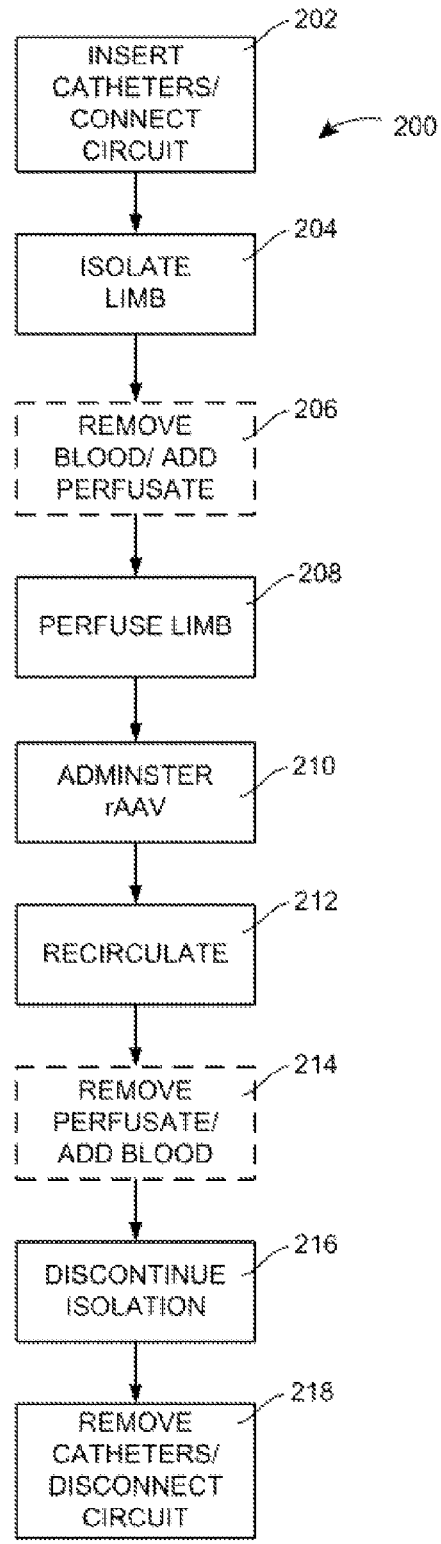
FIG. 6 is a flowchart of a method of recirculating rAAV according to the present disclosure.

By using the femoral artery delivery approach described in Example 4, vector escape outside the limb was minimized as shown by PCR-based detection of AAV vector genomes in organs throughout the body at the time of animal necropsy. FIG. 6 shows vector biodistribution data from fifteen monkeys receiving vector through the femoral artery. Only the targeted muscle (gastrocnemius) and spleen shows significant number of vector genomes. These samples were obtained three weeks post-gene delivery through the femoral artery. The number of vector genomes recovered from remote sites were negligible (note the log scale).

Example 6

Dose Escalation Study

A dose escalation study of AAVrh74.tMCK.hSGCA delivered via the femoral artery to the quadriceps muscles of both legs of LGMD2D (alpha-sarcoglycan-deficient) patients is performed. Two cohorts undergo gene transfer in a standard three-six dose escalation scheme to establish maximum tolerated dose (MTD) using toxicity. A minimum of three subjects are enrolled into each cohort. The first cohort receives a total dose of $3\times10^{13}$ vg split between the two extremities ($1.5\times10^{13}$ vg per limb). The vector is infused through the femoral artery using a percutaneous balloon catheter. This is a one-time vector infusion. The second cohort receives $1\times10^{14}$ vg total dose—split between the two quads ($5\times10^{13}$ vg per limb) delivered to the quadriceps muscles according to the same protocol. All patients undergo a muscle biopsy at 3 months (one leg), and 6 months (contra lateral leg) post-gene therapy.

More specifically, patients receive general anesthesia during the procedure. Procedures are performed under sterile conditions. The femoral arteries are catheterized percutaneously in the groin. A fluoroscopy guided 5 Fr catheter is advanced to the vessels supplying the quadriceps muscle. A blood pressure cuff at the knee serves as a tourniquet to promote vector delivery to the quadriceps muscles. A balloon catheter prevents backflow of vector to general circulation. Blood flow to the extremity is occluded for 10 minutes to promote transport through the endovascular barrier. Prior to vector administration, a pre-vector flush of saline (2.5 ml/kg) is given over one minute, immediately followed by occluding blood flow to the extremity. AAVrh.74.tMCK.hSGCA is infused over 60 seconds at a dose of $1.5\times10^{13}$ vg per limb in 2.5 ml/kg of Tris buffered saline for the low-dose cohort, and $5\times10^{13}$ vg per limb in 2.5 ml/kg of Tris buffered saline for the higher dose cohort. The extremity remains isolated from the circulation for 10 minutes before releasing the tourniquet. A post-vector flush (2.5 ml/kg) is infused over one minute prior to release of tourniquets. Direct pressure is applied for 10 minutes to ensure hemostasis.

Patients undergo muscle biopsies at two time points, three and six months (on contralateral limbs). Biopsy evaluation includes analysis of alpha-sarcoglycan expression and the entire sarcoglycan complex by immune stains and western blots. Mononuclear cells (CD4+ and CD8+, macrophages) are assessed as is MHC I and II expression. On a monthly basis, patents are evaluated for neutralizing antibodies to rAAV8 along with ELISpots to both rh.74 capsid and alpha-sarcoglycan protein. Muscle strength of the quadriceps is evaluated by quantitative myometry and timed functional tests of standing from a sitting position and walking 9 meters.

Example 7

Isolated Whole Limb Re-Circulation (IWLRC) Protocol

Some chemotherapeutic agents have been delivered by limb perfusion as described in Justison et al., *JECT,* 41: 231-234 (2009) and van Akkooi et al., *Eur. J. Cardiothoracic Surgery,* 30: 408-410 (2006). It is contemplated herein that recombinant viruses of the invention can also be delivered to a patient via a re-circulating methodology. The methodology provides controlled dwell time for viral uptake, control of perfusion pressure, vascular pH, vascular oxygenation and clearing of plasma/blood containing antibodies and complement from the targeted circulation and tissue. In brief, a limb of a patient is isolated with a tourniquet, an artery and vein of the limb are accessed with angio-catheters and the two catheters are connected via tubing, stopcocks and a pump. Buffered solution is pumped into the artery and blood and serum is collected from the limb into a sterile bag for redelivery upon completion of the procedure. While the limb is perfused with buffered solution, the viral vector is administered.

More specifically, to deliver AAVrh.74.tMCK.hSGCA to a lower limb of a patient for example, the patient is sedated and anesthetized. The inguinal area is prepared and draped in the usual sterile fashion. Appropriately sized angio-catheters are placed via direct cut down and blunt dissection into the femoral artery and vein at a site just distal to the inguinal ligament allowing enough space to place a tourniquet. The tourniquet allows temporary isolation of the lower extremity. Alternatively, it is contemplated that angio-catheters can be placed percutaneously or at distal sites and targeted by fluoroscopy.

To these angio-catheters a sterile 3/16" (ID) venous line is connected to the venous catheter with a luer lock. The tubing will contain two 3/16" single luer connectors separated by a three-inch piece of 3/16" tubing. Each 3/16" luer connector will have an associated six-inch pigtail and two-way stopcock. This allows for collection of the blood as it is displaced with a Normosol-R (Hospira Inc., Lake Forest, Ill.) solution. The blood will be mixed with 8 ml ACD-A anticoagulant during collection so that it may be returned post-procedure. From the second 3/16" double luer connector is again be 3/16" tubing that is placed within one of the roller-heads of a Maqet HL-20 twin roller pump (Maquet, Hirrlingen, Germany). This roller-head serves as the perfusate pump during the experiment. Post roller-head the 3/16" tubing is connected to a Sorin CSC 14 heat exchanger (Sorin Group USA, Inc., Arvada, Colo.) (28 ml prime volume). The CSC 14 allows for temperature regulation of the perfusate throughout the procedure. A two-inch piece of 3/16" tubing is connected to the outlet of the CSC 14 heat exchanger where a 3/16" single luer connector and associated six-inch pigtail and stopcock are connected. A two-inch piece of 3/16" tubing is connected to the opposite end of the 3/16" single luer and is then stepped down to 1/8" (ID) tubing that serves as the return line. The return line is connected to the catheter within the artery with a luer connection. All components are primed with Normosol-R in a sterile manner, and warmed to 37 degrees Celsius prior to connection with the arterial and venous catheters by recirculating through a bag of Normosol-R. The total prime volume of all components is 62 mL+/−10 mL.

Once connected to the venous and arterial cannulas, a tubing clamp is placed between the two 3/16" luer connectors on the venous limb. Normosol-R is injected into the distal luer connector utilizing a 60 mL syringe, displacing the blood into a 60 mL syringe (containing 8 mL ACD-A) attached to the proximal 3/16" luer. This process is repeated until the drainage (blood+Normosol) have an immeasurable hematocrit (<6 g/dL). The tubing clamp is removed and limb perfusion with AAVrh.74.tMCK.hSGCA begins. During limb perfusion, venous (drain) pressure is monitored utilizing a disposable pressure transducer connected to the HL-20 pump and to one of the 3/16" luer connectors within the venous line. The pressure is not allowed to be less than −50 mmHg. To insure the pressure does not go more negative than this, servo regulation of the pump is set to −50 mmHg. As the pressure approaches this pressure, the roller-head automatically slows or stops preventing damage to the vessel. Arterial (return) pressure monitoring is completed in the same manner on the 3/16" luer connector on the return line. This servo regulation is set to 200 mmHg. The perfusion flow rate is set at 50 mL/min and maintained for one hour.

At the conclusion of one hour of re-circulation, the blood and Normosol-R initially withdrawn during the connection process will be returned. To achieve this, a tubing clamp is placed between the two 3/16" luer connectors on the venous limb. An empty 60 mL syringe is connected to the proximal luer connector. The 60 mL syringes collected earlier are connected and injected via the distal luer connector in reverse order of their collection. Once the blood has been returned, the circuit is disconnected from the luer connectors and disposed of as biohazard waste. The tourniquet is removed slowly to allow systemic circulation to the limb and the cannulae removed. Pressure is used to control bleeding at the cut down site. Following the procedure, the patient is recovered in an appropriately warmed environment.

Example 8

IWLRC in the Non-Human Primate with a Reporter Construct

IWLRC with AAVrh.74 and a reporter transgene construct comprising a cytomegalovirus promoter and eGFP (AAVrh.74.CMV.eGFP) demonstrates efficiently expressed transgene with broad distribution throughout the major muscles of the lower limb.

Two vector/transgene doses, high $6\times10^{12}$ vg/kg and low $2\times10^{12}$ vg/kg, were administered to the lower extremities of two rhesus macaques, such that one animal received the low dose to both lower limbs and the other animal received the high dose to both lower limbs. Results achieved with the doses are presented in FIGS. 7 and 8, respectively.

On analysis of the major muscles of the lower extremity, both doses show broad transgene expression throughout the lower extremity with broader and more efficient expression in the lower extremity of the higher dosed animal. At the dose of $6\times10^{12}$, IWLRC resulted in greater than 40% muscle fiber transgene expression in major muscles of the lower extremity except the biceps femoris (HBF) and gracilis (HGras) of the Hamstring muscle group. Included in the graphs but not specifically targeted in this protocol as part of the lower limb are the Gluteus (max and med) muscles; broad expression in the gluteus medius and less in the gluteus maximus is noted.

Example 9

IWLRC in the Non-Human Primate with Therapeutic Transgenes

IWLRC was performed in non-human primates using AAVrh.74 to deliver a therapeutic micro-dystrophin transgene or a therapeutic alpha-sarcoglycan transgene (specifically using AAVrh.74.tMCK.hSGCA). Results achieved with the transgenes are presented in FIGS. 9 and 10, respectively.

The transgenes were expressed with broad distribution throughout the major muscles of the lower limb.

Example 10

Vascular Delivery of AAVrh.74.tMCK.hSGCA to Alpha-Sarcoglycan Knock-Out Mice

A two-dose escalation study was performed in alpha-sarcoglycan knock-out mice. The two doses were $6\times10^{11}$ vg/kg (low) and $2\times10^{12}$ vg/kg (high). The femoral artery of mice was catheterized and AAV74.tMCK.hSGCA was delivered at high or low dose in 100 μl. A tourniquet placed mid-thigh contained vector delivery to the lower extremity, limiting delivery to the lower limb muscles. Three months post-gene transfer, lower limb muscles were harvested and assessed for resistance to eccentric contraction based injury and tetanic force.

Figure 11:
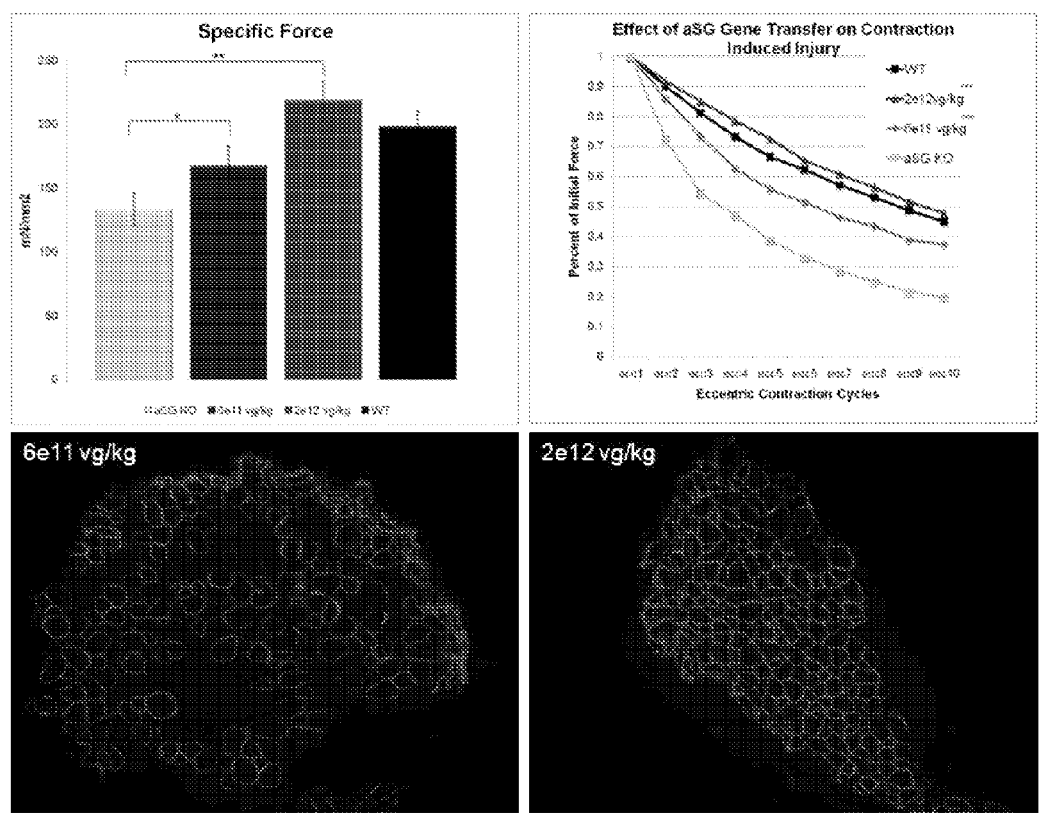
FIG. 11 shows rAAV.rh.74.tMCK.SGCA gene transfer restores specific force and resistance to eccentric contractions in the EDL of alpha-sarcoglycan knock-out mice. Alpha-sarcoglycan knock-out mice (n=12 per group) were treated by ILP at high ($2 \times 10^{12}$ vg/kg) and low ($6 \times 10^{11}$ vg/kg) doses.

Efficacy was demonstrated at both high and low dose. There was significant improvement versus alpha-sarcoglycan knock-out controls at both high and low dose. The high dose was not significantly different than wild-type mice (ANOVA). See FIG. 11.

While the present invention has been described in terms of specific embodiments, it is understood that variations and modifications will occur to those skilled in the art. Accordingly, only such limitations as appear in the claims should be placed on the invention.

All documents referred to in this application are hereby incorporated by reference in their entirety.

SEQUENCE LISTING

<160> NUMBER OF SEQ ID NOS: 5

<210> SEQ ID NO 1
<211> LENGTH: 2217
<212> TYPE: DNA
<213> ORGANISM: Adeno-Associated Virus rh.74

<400> SEQUENCE: 1

```
atggctgccg atggttatct tccagattgg ctcgaggaca acctctctga gggcattcgc    60
gagtggtggg acctgaaacc tggagccccg aaacccaaag ccaaccagca aaagcaggac   120
aacggccggg gtctggtgct tcctggctac aagtacctcg gaccctcaa cggactcgac    180 aagggggagc ccgtcaacgc ggcggacgca gcggccctcg agcacgacaa ggcctacgac   240
cagcagctcc aagcgggtga caatccgtac ctgcggtata tcacgccga cgccgagttt   300 caggagcgtc tgcaagaaga tacgtctttt ggggcaacc tcgggcgcgc agtcttccag    360
gccaaaaagc gggttctcga acctctgggc ctggttgaat cgccggttaa gacggctcct   420
ggaaagaaga gaccggtaga gccatcaccc cagcgctctc cagactcctc tacgggcatc   480
ggcaagaaag gccagcagcc cgcaaaaaag agactcaatt ttgggcagac tggcgactca   540
gagtcagtcc ccgaccctca accaatcgga gaaccaccag caggcccctc tggtctggga   600
tctggtacaa tggctgcagg cggtggcgct ccaatggcag acaataacga aggcgccgac   660
ggagtgggta gttcctcagg aaattggcat tgcgattcca catggctggg cgacagagtc   720
atcaccacca gcacccgcac ctgggcctg cccacctaca caaccacct ctacaagcaa   780 atctccaacg gacctcggg aggaagcacc aacgacaaca cctacttcgg ctacagcacc   840 ccctggggt attttgactt caacagattc cactgccact tttcaccacg tgactggcag    900
cgactcatca caacaactg gggattccgg cccaagaggc tcaacttcaa gctcttcaac   960
atccaagtca aggaggtcac gcagaatgaa ggcaccaaga ccatcgccaa taaccttacc  1020
agcacgattc aggtctttac ggactcggaa taccagctcc cgtacgtgct cggctcggcg  1080
caccagggct gcctgcctcc gttcccggcg gacgtcttca tgattcctca gtacgggtac  1140
ctgactctga acaatggcag tcaggctgtg ggccggtcgt ccttctactg cctggagtac  1200
tttccttctc aaatgctgag aacgggcaac aactttgaat tcagctacaa cttcgaggac  1260
gtgccctccc acagcagcta cgcgcacagc cagagcctgg accggctgat gaaccctctc  1320
atcgaccagt acttgtacta cctgtcccgg actcaaagca cgggcggtac tgcaggaact  1380
cagcagttgc tattttctca ggccgggcct aacaacatgt cggctcaggc caagaactgg  1440
ctacccggtc cctgctaccg gcagcaacgc gtctccacga cactgtcgca gaacaacaac  1500
agcaactttg cctggacggg tgccaccaag tatcatctga atggcagaga ctctctggtg  1560
aatcctggcg ttgccatggc tacccacaag gacgacgaag agcgattttt ccatccagc  1620 ggagtcttaa tgtttgggaa acaggagct ggaaagaca acgtggacta tagcagcgtg  1680
atgctaacca gcgaggaaga aataaagacc accaacccag tggccacaga acagtacggc  1740
```

```
gtggtggccg ataacctgca acagcaaaac gccgctccta ttgtaggggc cgtcaatagt   1800
caaggagcct tacctggcat ggtgtggcag aaccgggacg tgtacctgca gggtcccatc   1860
tgggccaaga ttcctcatac ggacggcaac tttcatccct cgccgctgat gggaggcttt   1920
ggactgaagc atccgcctcc tcagatcctg attaaaaaca cacctgttcc cgcggatcct   1980
ccgaccacct tcaatcaggc caagctggct tctttcatca cgcagtacag taccggccag   2040
gtcagcgtgg agatcgagtg ggagctgcag aaggagaaca gcaaacgctg gaacccagag   2100
attcagtaca cttccaacta ctacaaatct acaaatgtgg actttgctgt caatactgag   2160
ggtacttatt ccgagcctcg ccccattggc accgttacc tcacccgtaa tctgtaa     2217
```

```
<210> SEQ ID NO 2
<211> LENGTH: 738
<212> TYPE: PRT
<213> ORGANISM: Adeno-Associated Virus rh.74

<400> SEQUENCE: 2
```

```
Met Ala Ala Asp Gly Tyr Leu Pro Asp Trp Leu Glu Asp Asn Leu Ser
 1               5                  10                  15

Glu Gly Ile Arg Glu Trp Trp Asp Leu Lys Pro Gly Ala Pro Lys Pro
            20                  25                  30

Lys Ala Asn Gln Gln Lys Gln Asp Asn Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
 65                  70                  75                  80

Gln Gln Leu Gln Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
```

```
            290                 295                 300
Asn Asn Trp Gly Phe Arg Pro Lys Arg Leu Asn Phe Lys Leu Phe Asn
305                 310                 315                 320
Ile Gln Val Lys Glu Val Thr Gln Asn Glu Gly Thr Lys Thr Ile Ala
                325                 330                 335
Asn Asn Leu Thr Ser Thr Ile Gln Val Phe Thr Asp Ser Glu Tyr Gln
                340                 345                 350
Leu Pro Tyr Val Leu Gly Ser Ala His Gln Gly Cys Leu Pro Pro Phe
            355                 360                 365
Pro Ala Asp Val Phe Met Ile Pro Gln Tyr Gly Tyr Leu Thr Leu Asn
            370                 375                 380
Asn Gly Ser Gln Ala Val Gly Arg Ser Ser Phe Tyr Cys Leu Glu Tyr
385                 390                 395                 400
Phe Pro Ser Gln Met Leu Arg Thr Gly Asn Asn Phe Glu Phe Ser Tyr
                405                 410                 415
Asn Phe Glu Asp Val Pro Phe His Ser Ser Tyr Ala His Ser Gln Ser
                420                 425                 430
Leu Asp Arg Leu Met Asn Pro Leu Ile Asp Gln Tyr Leu Tyr Tyr Leu
            435                 440                 445
Ser Arg Thr Gln Ser Thr Gly Gly Thr Ala Gly Thr Gln Gln Leu Leu
            450                 455                 460
Phe Ser Gln Ala Gly Pro Asn Asn Met Ser Ala Gln Ala Lys Asn Trp
465                 470                 475                 480
Leu Pro Gly Pro Cys Tyr Arg Gln Gln Arg Val Ser Thr Thr Leu Ser
                485                 490                 495
Gln Asn Asn Asn Ser Asn Phe Ala Trp Thr Gly Ala Thr Lys Tyr His
                500                 505                 510
Leu Asn Gly Arg Asp Ser Leu Val Asn Pro Gly Val Ala Met Ala Thr
            515                 520                 525
His Lys Asp Asp Glu Glu Arg Phe Phe Pro Ser Ser Gly Val Leu Met
            530                 535                 540
Phe Gly Lys Gln Gly Ala Gly Lys Asp Asn Val Asp Tyr Ser Ser Val
545                 550                 555                 560
Met Leu Thr Ser Glu Glu Ile Lys Thr Thr Asn Pro Val Ala Thr
                565                 570                 575
Glu Gln Tyr Gly Val Val Ala Asp Asn Leu Gln Gln Asn Ala Ala
            580                 585                 590
Pro Ile Val Gly Ala Val Asn Ser Gln Gly Ala Leu Pro Gly Met Val
            595                 600                 605
Trp Gln Asn Arg Asp Val Tyr Leu Gln Gly Pro Ile Trp Ala Lys Ile
            610                 615                 620
Pro His Thr Asp Gly Asn Phe His Pro Ser Pro Leu Met Gly Gly Phe
625                 630                 635                 640
Gly Leu Lys His Pro Pro Gln Ile Leu Ile Lys Asn Thr Pro Val
                645                 650                 655
Pro Ala Asp Pro Pro Thr Thr Phe Asn Gln Ala Lys Leu Ala Ser Phe
                660                 665                 670
Ile Thr Gln Tyr Ser Thr Gly Gln Val Ser Val Glu Ile Glu Trp Glu
            675                 680                 685
Leu Gln Lys Glu Asn Ser Lys Arg Trp Asn Pro Glu Ile Gln Tyr Thr
            690                 695                 700
Ser Asn Tyr Tyr Lys Ser Thr Asn Val Asp Phe Ala Val Asn Thr Glu
705                 710                 715                 720
```

Gly Thr Tyr Ser Glu Pro Arg Pro Ile Gly Thr Arg Tyr Leu Thr Arg
            725                 730                 735

Asn Leu

<210> SEQ ID NO 3
<211> LENGTH: 1164
<212> TYPE: DNA
<213> ORGANISM: Homo sapiens

<400> SEQUENCE: 3

| | | | | | |
|---|---|---|---|---|---|
| atggccgaga | cactgttctg | gactcctctg | ctggtggtgc | tgctggctgg | actgggagat | 60 |
| accgaggctc | agcagaccac | actgcaccca | ctggtgggcc | gggtgttcgt | gcacaccctg | 120 |
| gaccatgaga | catttctgag | tctgccagaa | cacgtggctg | tgccacctgc | tgtgcatatc | 180 |
| acttaccacg | cccatctgca | gggccatcct | gatctgccac | ggtggctgag | atacacccag | 240 |
| agatcacccc | accatcctgg | attcctgtat | ggaagcgcta | ccccagagga | caggggactg | 300 |
| caggtgatcg | aagtgacagc | ttacaaccgc | gacagttttg | atactaccag | gcagcgcctg | 360 |
| gtgctggaga | ttggggatcc | agaaggaccc | ctgctgcctt | atcaggccga | gttcctggtg | 420 |
| cggtcacacg | acgctgagga | agtgctgcca | tcaacacccg | ccagcagatt | tctgtccgct | 480 |
| ctggaggac | tgtgggagcc | aggagaactg | cagctgctga | atgtgactag | cgctctggat | 540 |
| aggggaggaa | gggtgccact | gccaatcgag | ggaaggaagg | aagggtgta | cattaaagtg | 600 |
| ggaagcgctt | ccccattctc | cacctgcctg | aagatggtgg | cttctcctga | tagtcacgct | 660 |
| aggtgcgctc | agggacagcc | accactgctg | tcctgttatg | acacactggc | ccccattt | 720 |
| cgcgtggact | ggtgcaacgt | gactctggtg | gataaatctg | tgcctgagcc | agctgacgaa | 780 |
| gtgccaaccc | ctggagacgg | aatcctggag | cacgatcctt | tcttttgtcc | tccaacagaa | 840 |
| gccccagaca | gggatttcct | ggtggacgct | ctggtgactc | tgctggtgcc | tctgctggtg | 900 |
| gctctgctgc | tgaccctgct | gctggcttat | gtgatgtgct | gtcggagaga | gggacggctg | 960 |
| aagagagacc | tggccacatc | tgatatccag | atggtgcacc | attgtactat | tcacggcaac | 1020 |
| accgaggaac | tgcgccagat | ggctgcttct | agggaggtgc | caaggccact | gagtacactg | 1080 |
| cctatgttta | atgtgcacac | tggcgaacgg | ctgcccccta | gagtggatag | cgcccaggtg | 1140 |
| ccactgattc | tggaccagca | ttga | | | | 1164 |

<210> SEQ ID NO 4
<211> LENGTH: 738
<212> TYPE: PRT
<213> ORGANISM: Adeno-Associated Virus 8

<400> SEQUENCE: 4

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
                20                  25                  30

Lys Ala Asn Gln Gln Lys Gln Asp Asn Gly Arg Gly Leu Val Leu Pro
            35                  40                  45

Gly Tyr Lys Tyr Leu Gly Pro Phe Asn Gly Leu Asp Lys Gly Glu Pro
        50                  55                  60

Val Asn Ala Ala Asp Ala Ala Ala Leu Glu His Asp Lys Ala Tyr Asp
65                  70                  75                  80

Gln Gln Leu Gln Ala Gly Asp Asn Pro Tyr Leu Arg Tyr Asn His Ala
                85                  90                  95

-continued

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Ser Pro Val Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Asn Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

```
Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Gln Ile Leu Ile Lys Asn Thr Pro Val
                645                 650                 655

Pro Ala Asp Pro Pro Thr Thr Phe Asn Gln Ala Lys Leu Ala Ser Phe
                660                 665                 670

Ile Thr Gln Tyr Ser Thr Gly Gln Val Ser Val Glu Ile Glu Trp Glu
            675                 680                 685

Leu Gln Lys Glu Asn Ser Lys Arg Trp Asn Pro Glu Ile Gln Tyr Thr
        690                 695                 700

Ser Asn Tyr Tyr Lys Ser Thr Asn Val Asp Phe Ala Val Asn Thr Glu
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 5
<211> LENGTH: 4472
<212> TYPE: DNA
<213> ORGANISM: Adeno-Associated Virus rh.74

<400> SEQUENCE: 5
ctccatcact agggqtaacc gcgaagcgcc tcccacgctg ccgcgtcagc gctgacgtaa      60
attacgtcat aggggagtgg tcctgtatta gctgtcacgt gagtgctttt gcgacatttt     120
gcgacaccac gtggccattc atggtatata tggccgagtg agcgagcagg atctccattt     180
tgaccgcgaa atttgaacga gcagcagcca tgccgggctt ctacgagatc gtgcttaagg     240
tgccgagcga cctggacgag cacctgccgg gcatttctga ctcgtttgtg aactgggtgg     300
cagagaagga atgggagctg cccccggatt ctgacatgga tcggaatctg attgagcagg     360 caccctgac cgtggccgag aagctacagc gcgacttcct ggtccaatgg cgccgcgta     420 gtaaggcccc ggaggccctc ttctttgttc agttcgagaa gggcgagtcc tacttccacc     480
tccatattct ggtagagacc acggggtca atccatggt gctgggccgc ttcctgagtc     540
agattcggga caagctggtg cagaccatct accgcgggat cgagccgacc ctgcccaact     600
ggttcgcggt gacaaagacg cgtaatggcg ccggaggggg gaacaaggtg gtggacgagt     660
gctacatccc caactacctg ctgcccaaga ctcagcccga gctgcagtgg gcgtggacta     720
acatggagga gtatataagc gcgtgcttga acctggccga gcgcaaacgg ctcgtggcgc     780
agcacctgac ccacgtcagc cagacccagg agcagaacaa ggagaatctg aacccgaatt     840
```

```
ctgacgcgcc tgtcatccgg tcaaaaacct ccgcgcgcta catggagctg gtcgggtggc    900
tggtggaccg gggcatcacc tccgagaagc agtggatcca ggaggaccag gcctcgtaca    960
tctccttcaa cgccgcctcc aactcgcggt ctcagatcaa ggccgcgctg acaatgccg    1020
gcaagatcat ggcgctgacc aaatccgcgc ccgactacct ggtaggcccc gctctgcccg   1080
cggacattaa atccaaccgc atctaccgca tcctggagct gaatggctac gaccctgcct   1140
acgccggttc cgtctttctc ggctgggccc agaaaaagtt tggcaaaagg aacaccatct   1200
ggctgtttgg gccggccacc acgggcaaga ccaacatcgc ggaagccatc gcccacgccg   1260
tgcccttcta cggctgcgtc aactggacca atgagaactt cccttcaac gattgcgtcg    1320
acaagatggt gatctggtgg gaggagggca agatgacggc caaggtcgtg gagtccgcca   1380
aggccattct cggcggcagc aaggtgcgcg tggaccaaaa gtgcaagtcg tccgcccaga   1440
tcgatcccac ccccgtgatc gtcacctcca acaccaacat gtgcgccgtg attgacggga   1500
acagcaccac cttcgagcac cagcagccgt gcaggaccg gatgttcaaa tttgaactta    1560
cccgccgtct ggagcacgac tttggcaagg tgacaaagca ggaagtcaaa gagttcttcc   1620
gctgggcgca ggatcacgtg accgaggtgg cgcatgagtt ctacgtcaga aagggtggag   1680
ctaacaaaag acccgccccc gatgacgcgg atataagcga gcccaagcgg gcctgcccct   1740
cagtcgcgga tccatcgacg tcagacgcgg aaggagctcc ggtggacttt gccgacaggt   1800
accaaaacaa atgttctcgt cacgcgggca tgcttcagat gctgtttccc tgcaaaacat   1860
gcgagagaat gaatcagaat ttcaacattt gcttcacgca cgggaccaga gactgttcag   1920
aatgtttccc tggcgtgtca gaatctcaac cggtcgtcag aaaaaagacg tatcggaaac   1980
tctgtgcgat tcatcatctg ctggggcggg cacccgagat tgcttgctcg gcctgcgacc   2040
tggtcaacgt ggacctggat gactgtgttt ctgagcaata aatgacttaa accaggtatg   2100
gctgccgatg gttatcttcc agattggctc gaggacaacc tctctgaggg cattcgcgag   2160
tggtgggacc tgaaacctgg agccccgaaa cccaaagcca accagcaaaa gcaggacaac   2220
gccggggtc tggtgcttcc tggctacaag tacctcggac ccttcaacgg actcgacaag    2280
ggggagcccg tcaacgcggc ggacgcagcg gccctcgagc acgacaaggc ctacgaccag   2340
cagctccaag cgggtgacaa tccgtacctg cggtataatc acgccgacgc cgagtttcag   2400
gagcgtctgc aagaagatac gtcttttggg gcaacctcg gcgcgcagt cttccaggcc    2460
aaaaagcggg ttctcgaacc tctgggcctg gttgaatcgc cggttaagac ggctcctgga   2520
aagaagagac cggtagagcc atcacccag cgctctccag actcctctac gggcatcggc    2580
aagaaaggcc agcagcccgc aaaaaagaga ctcaattttg gcagactgg cgactcagag    2640
tcagtccccg accctcaacc aatcggagaa ccaccagcag gccctctgg tctgggatct    2700
ggtacaatgg ctgcaggcgg tggcgctcca atggcagaca ataacgaagg cgccgacgga   2760
gtgggtagtt cctcaggaaa ttggcattgc gattccacat ggctgggcga cagagtcatc   2820
accaccagca cccgcacctg ggccctgccc acctacaaca accacctcta caagcaaatc   2880
tccaacggga cctcgggagg aagcaccaac gacaacacct acttcggcta cagcaccccc   2940
tgggggtatt ttgacttcaa cagattccac tgccactttt caccacgtga ctggcagcga   3000
ctcatcaaca caactgggg attccggccc aagaggctca acttcaagct cttcaacatc    3060
caagtcaagg aggtcacgca gaatgaaggc accaagacca tcgccaataa ccttaccagc   3120
acgattcagg tctttacgga ctcggaatac cagctcccgt acgtgctcgg ctcggcgcac   3180
```

```
cagggctgcc tgcctccgtt cccggcggac gtcttcatga ttcctcagta cgggtacctg    3240
actctgaaca atggcagtca ggctgtgggc cggtcgtcct tctactgcct ggagtactt     3300 ccttctcaaa tgctgagaac gggcaacaac tttgaattca gctacaactt cgaggacgtg    3360
cccttccaca gcagctacgc gcacagccag agcctggacc ggctgatgaa ccctctcatc    3420
gaccagtact tgtactacct gtcccggact caaagcacgg gcggtactgc aggaactcag    3480
cagttgctat tttctcaggc cgggcctaac aacatgtcgg ctcaggccaa gaactggcta    3540
cccggtccct gctaccggca gcaacgcgtc tccacgacac tgtcgcagaa caacaacagc    3600
aactttgcct ggacgggtgc caccaagtat catctgaatg gcagagactc tctggtgaat    3660
cctggcgttg ccatggctac ccacaaggac gacgaagagc gatttttttcc atccagcgga   3720 gtcttaatgt ttgggaaaca gggagctgga aaagacaacg tggactatag cagcgtgatg    3780
ctaaccagcg aggaagaaat aaagaccacc aacccagtgg ccacagaaca gtacggcgtg    3840
gtggccgata acctgcaaca gcaaaacgcc gctcctattg tagggccgt caatagtcaa      3900 ggagccttac ctggcatggt gtggcagaac cgggacgtgt acctgcaggg tcccatctgg    3960
gccaagattc ctcatacgga cggcaacttt catccctcgc cgctgatggg aggctttgga    4020
ctgaagcatc cgcctcctca gatcctgatt aaaaacacac ctgttcccgc ggatcctccg     4080
accaccttca atcaggccaa gctggcttct ttcatcacgc agtacagtac cggccaggtc    4140
agcgtggaga tcgagtggga gctgcagaag gagaacagca aacgctggaa cccagagatt    4200
cagtacactt ccaactacta caaatctaca aatgtggact ttgctgtcaa tactgagggt    4260
acttattccg agcctcgccc cattggcacc cgttacctca cccgtaatct gtaattacat    4320
gttaatcaat aaaccggtta attcgtttca gttgaacttt ggtctcctgt ccttcttatc    4380
ttatcggtta ccatagaaac tggttactta ttaactgctt ggtgcgcttc gcgataaaag    4440
acttacgtca tcgggttacc cctagtgatg ga                                  4472
```

We claim:

1. A method of improving muscle function in a patient afflicted with limb girdle muscular dystrophy type 2D (LGMD 2D) comprising the step of perfusing the vasculature of a limb of the patient with an infectious encapsidated recombinant adeno-associated virus (AAV) comprising a AAVrh.74 capsid polynucleotide of SEQ ID NO:2, wherein the genome of the recombinant AAV comprises a gene expression cassette comprising the polynucleotide of SEQ ID NO: 3 encoding an alpha-sarcoglycan under the transcriptional control of a promoter, said cassette flanked by one or more AAV inverted terminal repeats, and wherein the genome lacks AAV rep and cap DNA.

2. A method of delivering an alpha-sarcoglycan polynucleotide to an animal in need thereof, comprising the step of perfusing the vasculature of a limb of the animal with an infectious encapsidated recombinant AAV comprising a AAVrh.74 capsid polynucleotide of SEQ ID NO:2, wherein the genome of the recombinant AAV comprises a gene expression cassette comprising the polynucleotide of SEQ ID NO: 3 encoding an alpha-sarcoglycan under the transcriptional control of a promoter, said cassette flanked by one or more AAV inverted terminal repeats, and wherein the genome lacks AAV rep and cap DNA.

3. An infectious encapsidated recombinant AAV comprising a AAVrh.74 capsid polynucleotide of SEQ ID NO: 2, wherein the genome of the recombinant AAV comprises a gene expression cassette comprising the polynucleotide of SEQ ID NO: 3 encoding an alpha-sarcoglycan under the transcriptional control of a promoter, said cassette flanked by one or more AAV inverted terminal repeats, and wherein the genome lacks AAV rep and cap DNA.

4. A method of delivering a recombinant adeno-associated virus (AAV) comprising:
connecting a recirculation circuit to a vasculature of a limb;
isolating circulation of the limb from the remainder of the body;
adding to the recirculation circuit an infectious encapsidated recombinant AAV comprising a AAVrh.74 capsid polynucleotide of SEQ ID NO:2, wherein the genome of the recombinant AAV comprises a gene expression cassette comprising the polynucleotide of SEQ ID NO: 3 encoding an alpha-sarcoglycan under the transcriptional control of a promoter, said cassette flanked by one or more AAV inverted terminal repeats, and wherein the genome lacks AAV rep and cap DNA;
passing the recombinant AAV through the recirculation circuit and the limb repeatedly; and
disconnecting the recirculation circuit from the limb.

5. The method of claim 4, further comprising:
removing a volume of blood from the limb after isolating the limb from the remainder of the body;
introducing a non-blood perfusate to the recirculation circuit and the limb prior to adding the recombinant AAV to the recirculation circuit; and passing the non-blood perfusate through the recirculation circuit and the limb repeatedly as the recombinant AAV is passed through the recirculation circuit and the limb.

6. The method of claim 5, wherein the non-blood perfusate comprises a buffer solution.

7. The method of claim 5, further comprising:
removing the non-blood perfusate after repeatedly passing the recombinant AAV and the non-blood perfusate through the recirculation circuit and the limb; and
reintroducing the volume of blood to the limb after removing the non-blood perfustate.

* * * * *

UNITED STATES PATENT AND TRADEMARK OFFICE
CERTIFICATE OF CORRECTION

PATENT NO. : 9,434,928 B2  
APPLICATION NO. : 14/360243  
DATED : September 6, 2016  
INVENTOR(S) : Jerry R. Mendell et al.

It is certified that error appears in the above-identified patent and that said Letters Patent is hereby corrected as shown below:

In the Claims

At Column 35, Line 46, delete "polynucleotide".

At Column 37, Line 11, "perfustate." should be -- perfusate. --.

Signed and Sealed this  
Sixth Day of November, 2018

Andrei Iancu  
*Director of the United States Patent and Trademark Office*

UNITED STATES PATENT AND TRADEMARK OFFICE
CERTIFICATE OF CORRECTION

PATENT NO. : 9,434,928 B2  
APPLICATION NO. : 14/360243  
DATED : September 6, 2016  
INVENTOR(S) : Jerry R. Mendell et al.

Page 1 of 1

It is certified that error appears in the above-identified patent and that said Letters Patent is hereby corrected as shown below:

In the Claims

Column 35, Line 57, delete "polynucleotide".

Column 35, Line 65, delete "polynucleotide".

Column 36, Line 52, delete "polynucleotide".

Signed and Sealed this  
Seventh Day of July, 2020

Andrei Iancu  
*Director of the United States Patent and Trademark Office*